(12) United States Patent
Ignatius et al.

(10) Patent No.: US 9,012,204 B2
(45) Date of Patent: Apr. 21, 2015

(54) ACTIVATION AND MONITORING OF CELLULAR TRANSMEMBRANE POTENTIALS

(75) Inventors: Michael J. Ignatius, Eugene, OR (US); Elena Molokanova, Eugene, OR (US); Alexei Savtchenko, Eugene, OR (US); Joseph A. Bartel, Eugene, OR (US); Weiwen Zhao, Eugene, OR (US); Joseph A. Treadway, Eugene, OR (US)

(73) Assignee: Life Technologies Corporation, Carlsbad, CA (US)

( * ) Notice: Subject to any disclaimer, the term of this patent is extended or adjusted under 35 U.S.C. 154(b) by 345 days.

(21) Appl. No.: 13/187,297

(22) Filed: Jul. 20, 2011
(Under 37 CFR 1.47)

(65) Prior Publication Data
US 2012/0034622 A1   Feb. 9, 2012

Related U.S. Application Data

(63) Continuation of application No. 12/996,354, filed as application No. PCT/US2009/046312 on Jun. 4, 2009, now abandoned.

(60) Provisional application No. 61/059,155, filed on Jun. 5, 2008.

(51) Int. Cl.
C12M 1/34 (2006.01)
G01N 33/68 (2006.01)
B82Y 5/00 (2011.01)
B82Y 15/00 (2011.01)
G01N 33/58 (2006.01)

(52) U.S. Cl.
CPC .............. *G01N 33/6872* (2013.01); *B82Y 5/00* (2013.01); *B82Y 15/00* (2013.01); *G01N 33/588* (2013.01); *G01N 2500/10* (2013.01)

(58) Field of Classification Search
None
See application file for complete search history.

(56) References Cited

U.S. PATENT DOCUMENTS

| | | | |
|---|---|---|---|
| 5,505,928 A | 4/1996 | Alivisatos et al. | |
| 5,990,479 A | 11/1999 | Weiss et al. | |
| 6,114,038 A | 9/2000 | Castro et al. | |
| 6,194,213 B1 | 2/2001 | Barbera-Guillem | |
| 6,207,229 B1 | 3/2001 | Bawendi et al. | |
| 6,207,392 B1 | 3/2001 | Weiss et al. | |
| 6,221,602 B1 * | 4/2001 | Barbera-Guillem et al. | 435/6.11 |
| 6,251,303 B1 | 6/2001 | Bawendi et al. | |
| 6,274,323 B1 | 8/2001 | Bruchez et al. | |
| 6,306,610 B1 | 10/2001 | Bawendi et al. | |
| 6,319,426 B1 | 11/2001 | Bawendi et al. | |
| 6,319,607 B1 * | 11/2001 | Barbera-Guillem et al. | 428/402.24 |

(Continued)

FOREIGN PATENT DOCUMENTS

WO   WO-01/59446   8/2001
WO   WO-2004/034025   4/2004

(Continued)

OTHER PUBLICATIONS

Paul (1980) Anal Biochem 101:442-448.*

(Continued)

*Primary Examiner* — Bao Thuy L Nguyen
*Assistant Examiner* — Richard Moerschell
(74) *Attorney, Agent, or Firm* — Life Technologies Corporation

(57) ABSTRACT

The use of nanostructures to monitor or modulate changes in cellular membrane potentials is disclosed.

17 Claims, 22 Drawing Sheets

(56) References Cited

U.S. PATENT DOCUMENTS

| | | | |
|---|---|---|---|
| 6,322,901 | B1 | 11/2001 | Bawendi et al. |
| 6,326,144 | B1 | 12/2001 | Bawendi et al. |
| 6,423,551 | B1 | 7/2002 | Weiss et al. |
| 6,426,513 | B1 | 7/2002 | Bawendi et al. |
| 6,444,143 | B2 | 9/2002 | Bawendi et al. |
| 6,500,622 | B2 | 12/2002 | Bruchez, Jr. et al. |
| 6,548,168 | B1 | 4/2003 | Mulvaney |
| 6,576,291 | B2 | 6/2003 | Bawendi et al. |
| 6,649,138 | B2 | 11/2003 | Adams et al. |
| 6,699,723 | B1 | 3/2004 | Weiss et al. |
| 6,815,064 | B2 | 11/2004 | Treadway et al. |
| 6,819,692 | B2 | 11/2004 | Klimov et al. |
| 6,821,337 | B2 | 11/2004 | Bawendi et al. |
| 6,921,496 | B2 | 7/2005 | Anderson et al. |
| 7,068,898 | B2 | 6/2006 | Buretea et al. |
| 7,079,241 | B2 | 7/2006 | Empedocles et al. |
| 7,108,915 | B2 | 9/2006 | Adams et al. |
| 7,138,098 | B2 | 11/2006 | Bawendi |
| 2004/0110123 | A1 | 6/2004 | Maher et al. |
| 2004/0134414 | A1* | 7/2004 | Lewis et al. ............... 117/2 |
| 2005/0117868 | A1* | 6/2005 | Chen et al. ............... 385/143 |
| 2008/0038771 | A1* | 2/2008 | Taylor et al. ............... 435/40.5 |
| 2008/0221310 | A1* | 9/2008 | O'Sullivan et al. ............... 530/412 |
| 2010/0116664 | A1 | 5/2010 | Ignatius et al. |
| 2010/0178665 | A1 | 7/2010 | Ignatius et al. |

FOREIGN PATENT DOCUMENTS

| | | | |
|---|---|---|---|
| WO | WO-2006/096835 | | 9/2006 |
| WO | WO 2006/096835 | * | 9/2006 |
| WO | WO-2006096835 | | 9/2006 |
| WO | WO-2010/002540 | | 1/2010 |

OTHER PUBLICATIONS

Kim 2003 Applied Physics Letters 83: 4619-4621.*

Pappas (2007) Nano ltr 7: 513-519.*

Alivisatos, A. P. "Perspectives on the Physical Chemistry of Semiconductor Nanocrystals", *The Journal of Physical Chemistry* 1996, vol. 100, No. 31, pp. 13226-13239.

Brueggemann, A. et al. "Ion Channel Drug Discovery and research: The Automated nano-Patch-Clamp Technology", *Current Drug Discovery Technologies*, 2004,1 (1), pp. 91-96.

Chan, C., et al. "Quantum Dot Bioconjugates for Ultrasensitive Nonisotopic Detection", Science,US,American Association for the Advancement of Science; 1998, vol. 281(281), pp. 2016-2018.

Dahan, M., et al. "Diffusion Dynamics of Glycine Receptors Revealed by Single-Quantum Dot Tracking", *Science*, 2003, 317(2), pp. 442-445.

Fromherz, P., et al. "Silicon-Neuron Junction: Capacitive Stimulationof an Individual Neuron on a Silicon Chip", *Phys. Rev. Lett.* 1995, pp. 1670-1673.

Gheith, M., et al. "Stimulation of Neural Cells by Lateral Currents in Conductive Layer-by-Layer Films of Single-Walled Carbon Nanotubes." *Adv. Mater*, 2006, 18 (22), pp. 2975-2979.

Hamill, "Improved patch-clamp techniques for high-resolution current recording from cells and cell-free membrane patches", *Pfulgers Arch.* vol. 391, No. 2, 1981 , 85-100.

Hao, E., et al. "Electromagnetic Fields Around Silver Nanoparticles and dimers", *Journal of Chem. Phy*, 2004, 120(1), pp. 357-366.

Hao, E., et al. "Synthesis and Optical Properties of Anisotropic Metal Nanoparticles", *Journal of Fluorescence*, 2004, 14(4), pp. 331-341.

Kagan, C., et al. "Long-range resonance transfer of electronic excitations in close-packed CdSe quantum-dot solids", *Physical Review B*, , 1996, vol. 54, No. 12, pp. 8633-8643.

Kloepfer, J. A. "Fret between CdSe quantum dots in lipid vesicles and water- and lipid-soluble dyes", *Journal of Physical Chemistry B 20041104 American Chemical Society US* vol. 108, No. 44 4 Nov. 2004 , 17042-17049.

Li, N. "Biology on a chip: Microfabrication for styding the behavior of cultured cells", *Critical Reviews in Biomedical Engineering* vol. 31, No. 5&6 2003 , 423-488.

Pap Pappas, T., et al. "Nanoscale Engineering of a Cellular Interface with Semiconductor Nanoparticle films fr Photoelectric Stimulation of Neurons." *Nano Letters*, 2007, 7(2), pp. 513-519.

International Search Report for PCT Application No. PCT/US09/046312 mailed Feb. 5, 2010.

International Preliminary Report on Patentability for PCT Application No. PCT/US09/46312 mailed Dec. 16, 2010.

Robel, I., et al. "Size-Dependent Electron Injection from Excited CdSe Quantum Dots into $TiO_{2\ \textit{1 Nanoparticles}}$," *J. Am Chem. Soc.*, 2007, 129, pp. 4136-4137.

Starovoytov, A., et al. "Light-Directed Electrical Stimulation of Neurons Cultured on Silicon Wafers", *J. of Neurophysiol*, 2004, 93, pp. 1090-1098.

Stroscio, M., et al. "Integrated biological-semiconductor devices", *Proceedings of the IEEE* 2005, 93(10) , pp. 1772-1783.

Watson, A., et al. "Lighting Up Cells with Quantum Dots", *Biotechniques*, 2003, 34 (2), pp. 296-303.

Weiss, E., et al. "Influence of Defects on the Electrical Characteristics of Mercury-Drop Junctions: Self-Assembled Monolayers o n-Akanethiolates on Rough and Smooth Silver."*J. Am. Chem. Soc.*, 2007, 129 (14), pp. 4336-4349.

Winter, J. O. "Development and Optimization of Quantum Dot-Neuron Interfaces", *Dissertation presented to the faculty of the graduate school of the University of Texas at Austin* 2004.

Winter, J., et al. "Optimization of quantum dot—Nerve cell interfaces", *Materials Research Society Symposium*, 2003, 789, pp. 119-122.

Winter, J. , et al. "Quantum dots for electrical stimulation of neural cells", *Progress in Biomedical Optics and Imaging of SPIE—Nanobiophotonics and Biomedical Applications SPIE US*, 2005, 5705, pp. 235-246.

Winter, J., et al. "Recognition molecule directed interfacing between semiconductor quantum dots and nerve cells", *Advanced Materials 20011116 Wiley-VCH Verlag DEU* 2001, 13 (22), pp. 1673-1677.

International Preliminary Report on Patentability for PCT Application No. PCT/US06/08560 mailed Sep. 12, 2007.

International Search Report for PCT Application No. PCT/US06/08560 mailed Sep. 13, 2006.

Zorov, D., et l. "Examining Intracellular Organelle Function Using Fluorescent Probes From Animalcules to Quantum Dots", *Circulation Research*, 2004, 95, pp. 239-252.

Jaiswal, J. et al., "Long-Term Multiple Color Imaging of Live Cells Using Quantum Dot Bioconjugates", *Nature Biotechnology*, Jan. 21, 2003, 47-51.

Molokanova, Elena et al., "Bright future of optical assays for ion channel drug discovery", *Drug Discovery Today*, Jan. 3, 2008, vol. 13, No. 1-2, 14-22.

Molokanova, Elena et al., "Quantum Dots Move Beyond Fluorescence Imaging", *Biophotonics International*, vol. 15, No. 6 Jun. 1, 2008, 26-31.

Pappas, T C et al., "Nanoscale engineering of a cellular interface with semiconductor nanoparticle films for photoelectric stimulation of neurons", *Nano Letters*, Feb. 1, 2007, vol. 7, No. 2, 513-519.

* cited by examiner

ACTIVATION AND MONITORING OF
CELLULAR TRANSMEMBRANE
POTENTIALS

CROSS REFERENCE TO RELATED APPLICATIONS

This application is a continuation of U.S. patent application Ser. No. 12/996,354, filed Dec. 3, 2010 now abandoned, which is a national phase application under 35 U.S.C. §371 of International Patent Application No. PCT/US09/46312, filed Jun. 4, 2009, which claims priority to U.S. Provisional Application No. 61/059,155, filed Jun. 5, 2008, the disclosures of which are hereby incorporated by reference in their entireties.

FIELD OF THE INVENTION

The invention relates to compositions and methods useful for monitoring and manipulating cellular transmembrane voltages. In particular, nanoparticles and their use in monitoring and manipulating transmembrane voltages are disclosed.

DESCRIPTION OF RELATED ART

Cells have phospholipid membranes that serve as bimolecular barriers that separate cell contents from the extracellular environment. The phospholipid membranes maintain the necessary compositional differences between cellular compartments and the extracellular milieu by regulating the passage of materials through the membrane as a function of intracellular signaling. The normally impermeable phospholipid membrane has a resting membrane potential originating from an unequal distribution of positively and negatively charged ions in the extracellular and intracellular compartments. The membrane potential can be changed by changing membrane permeability to a certain ion in response to an activating stimulus, thus allowing a flux of ions down their electrochemical gradient. See, e.g., co-owned and co-pending U.S. application Ser. No. 11/371,465, filed Mar. 8, 2006. Cells communicate with each other through changes in membrane potential. Therefore, monitoring the cellular membrane potential and its changes allows monitoring of cell viability, cell communication (e.g., particular neurons, muscle and other excitable cells) and cell function and differentiation.

Ion channels are transmembrane proteins present in the phospholipid membranes of both excitable and non-excitable cells. Ion channels permit and regulate movement and conduction of ions down their electrochemical gradients across the normally ion-impermeant lipid bilayer. The various states of ion channel activation provide unique opportunities for more efficient drug discovery, enabling state-dependent molecules to be developed that, for example, only bind to non-conducting (inactivated) channels, or channels whose behavior and structure changes after repeated use. A desirable goal is to target drugs to tissues exhibiting abnormal electrical activity, while leaving normal channels in active tissues unaffected.

Ion channels are of particular importance as drug targets and ion channel safety pharmacology. Ion channels are involved in many vital functions, and a dysfunction of ion channels caused by changes in biochemical regulation, expression levels, or structural mutations can adversely impact the well-being of living organisms. In humans, inherited or induced changes in ion channel function could result in serious complications to health. Abnormal ion channel function or ion channel expressions have been linked to a number of therapeutic areas including cardiac arrhythmia, hypertension, epilepsy, pain, cystic fibrosis, and episodic ataxias. There is an ongoing need for more effective ion channel modulator drugs for such diseases.

A variety of experimental approaches are used in ion channel research. For example, one method for studying ion channels is the patch clamp method (Neher, E., et al., *Nature* (1976) 260(5554):799-802; Hamill, O. P., et al., *Pflugers Arch.* (1981) 391(2):85-100). Although this technique allows some detailed biophysical characterization of ion channel physiology, throughput is quite low and ease-of-use of patch-clamp instrumentation is generally unsatisfactory for effective mass screening. Patch clamp instrumentation also does not allow for repeated stimulation of cells to generate action potential in a physiologically relevant manner. The demands of ion channel high throughput screening ("HTS") include robust instrumentation and high signal-background ratio combined with satisfactory ease-of-use. Historically, ion channel HTS is equated with low information content, emphasizing the need for novel rapid and easy methods in which more useful information can be gathered about membrane potential changes in various cell types.

Reliable and robust HTS assays for ion channels are important in ion-channel based drug discovery. Ion channels are dynamic proteins, and therefore require assays that "sense" their various functional states. Competition-binding assays, although successfully used for other target classes, often fail to identify ligands that modulate specific ion channel states. Cell-based functional assays, therefore, are preferred for HTS of ion channel targets.

Some of the HTS technologies employed for ion channel screening include: binding assays, ion flux assays, fluorometric imaging and electrophysiology. The HTS patch clamp technique is widely used to study currents through ion channels. The whole-cell patch-clamp is used today in tertiary screening of selected lead molecules in late stages of the drug discovery process. Whole-cell patch-clamp, however, is not suitable for initial high throughput screening. Although very powerful, this technique is labor-intensive and, therefore, limited to few data point measurements per day. This low throughput has encouraged the use of other less specific and less sensitive technologies for high-throughput screening of ion channel targets. Ideally, a robust HTS ion channel screening method would have high temporal resolution, high sensitivity and high information content, resulting in low rates of "false negatives" and "false positives". Despite the materials and methods available to study ion channels, there exists a need for new materials and methods that are easy, robust, and useful.

SUMMARY OF THE INVENTION

In one aspect, a method is provided for assaying or monitoring changes in transmembrane potential that comprises providing at least one target cell; contacting the target with at least one activation platform to form a treated target, wherein the activation platform comprises at least one layer of immobilized nanocrystals covered by at least one layer of adhesion substrate; stimulating the treated target; assaying emission from the activation platform; and correlating the emission with the change in transmembrane potential. The methods provided herein can use an activation platform that comprises two or more layers of immobilized nanocrystals. For example the activation platform can comprises about 2 to about 15 layers of immobilized nanocrystals. In certain embodiments, the activation platform can comprise about 5 to about 10 layers of immobilized nanocrystals.

In another aspect, a method for monitoring transmembrane potential is provided. The method comprises: providing at least one target cell; treating the target with nanocrystals embedded in the plasma membrane, creating a sensing platform to form a treated target, wherein the underlying activation platform comprises at least one layer of immobilized nanocrystals covered by at least one layer of adhesion substrate; stimulating the treated target; assaying emission from the sensing platform; and correlating the emission with the change (or lack thereof) in transmembrane potential.

In yet another aspect, a method for assaying or monitoring changes in transmembrane potential is provided, comprising: providing at least one target cell; contacting the target with at least one activation platform to form a treated target, wherein the activation platform comprises at least one layer of immobilized nanocrystals; stimulating the treated target; assaying emission from the activation platform; and correlating the emission with the change in transmembrane potential.

The stimulating step can comprise optical stimulation, electrical stimulation, magnetic stimulation, chemical stimulation, biological stimulation, contacting the target with a drug suspected of being able to activate ion channels, contacting the target with a drug suspected of being able to inhibit ion channels, or combinations thereof. In some embodiments, the electrical stimulation comprises use of a patch clamp, or application of an external electric field. In one embodiment, the chemical stimulation comprises contacting the target with a potassium salt or a sodium salt. In some embodiments, the biological stimulation comprises contacting the target with a light-sensitive ion channel.

The stimulating step can comprise maintaining the target at a first membrane potential voltage, depolarizing or hyperpolarizing the target to a second membrane potential voltage, and returning the target to the first membrane potential voltage. In some embodiments, the second membrane potential voltage is more positive than the first membrane potential voltage. In one embodiment, the second membrane potential voltage is positive, and the first membrane potential voltage is negative. In some embodiments, one of the first membrane potential voltage and the second membrane potential voltage is about 0 mV. In one embodiment, the first membrane potential voltage is about −70 mV and the second membrane potential voltage is about +40 mV.

The cell can be a eukaryotic cell, a prokaryotic cell, bacterial cell, a Gram-positive bacterial cell, a Gram-negative bacterial cell, a fungal cell, an insect cell, an avian cell, a reptilian cell, an oocyte, a fly cell, a zebrafish cell, a nematode cell, a fish cell, an amphibian cell, or a mammalian cell.

The structure for the activation platform can be a film, a nanowire, a patterned substrate, or a mesh. Typically, the nanocrystal is a quantum dot.

In some embodiments, the stimulating step comprises illuminating at a wavelength or wavelength range suitable for absorption by the activation platform. The stimulating step can comprise laser illumination, mercury lamp illumination, xenon lamp illumination, halogen lamp illumination, or LED illumination.

The assaying emission can be performed using optical detection. The optical detection comprises use of a camera, a digital camera, a video camera, a CCD camera, a digital camera mounted on a fluorescent microscope, a photomultiplier, a fluorometer, a luminometer, a microscope, or the human eye. The assaying step can comprise assaying or detecting at a single time point, at multiple time points, or continuous detection.

In another aspect, a method is provided for activating a cell. Further provided herein is an integrated optical assay that combines optical stimulation (via activation platforms) and an optical recording of cellular activity. Certain methods detect cellular activity using an ion sensitive dye. Any suitable method of optically recording cellular activity can be employed. Thus, the methods provided herein can further comprise an optical recording of cellular activity simultaneously or in coordination with assaying changes in transmembrane potential.

In one aspect, a light-controlled activation platform is provided that includes one or more type of nanomaterials (e.g., semiconductor nanocrystals). In certain embodiments, the nanomaterials are capable of functioning as optical voltage sensors. In other embodiments, the nanomaterials are capable of activating changes in cellular membrane potential. In certain embodiments, the nanomaterials comprise nanocrystals (e.g., semiconductor nanocrystals).

In another aspect, compositions are provided for monitoring and manipulating cellular transmembrane potentials, comprising: a substrate and an activation platform, wherein the activation platform is disposed on a surface of the substrate, wherein the activation platform comprises one or more layers of immobilized nanocrystals. In certain aspects, the activation platform comprises two or more types of nanocrystals, wherein the two or more types have different optical properties. The nanocrystals can be semiconductor nanocrystals. Each nanocrystal can comprise a semiconductor core. The semiconductor core can further comprise a coating on the core. The coating can comprise a hydrophilic compound. Each nanocrystal can further comprise a semiconductor shell between the core and the coating, such as a positively charged compound or a negatively charged compound. The nanocrystal can comprise a surface coating, wherein the coating comprises a material having one or more thiol, sulfonate, or carboxylate groups. The coating can comprise 1-thioglycerol, thioglycolic acid, 2-mercaptoethane sulfonate, poly(acrylic acid) or a derivative thereof, lipoic acid, dihydrolipoic acid, polyethylenimine, cysteamine, polyallylamine, histidine, polyhistidine, lysine, or polylysine. The activation platform can further comprise an adhesion substrate, and the adhesion substrate can comprise poly-L-lysine, fibronectin, collagen, elastin, hyaluronic acid, laminin, matrigel, lectins, antibodies to cellular membrane proteins, or RGD peptides and their progeny. The one or more layers of nanocrystals can further comprise a polymer, such as agarose, polymethyl methacylate, or polyacrylamide. The activation platform can comprise two or more layers of immobilized nanocrystals (e.g., about 2 to about 15 layers or about 5 to about 10 layers). The composition can further include one or more layers of an organic material, such as a polymer (e.g., a synthetic polymer). The polymer can be PDDA. In certain embodiments, the nanocrystals are water-dispersible.

In yet another aspect, a method of making an activation platform is provided, comprising providing a substrate; applying one or more layers of nanocrystals onto a surface of the substrate; and applying a cell adhesion layer onto the one or more layers of nanocrystals. The one or more layers of nanocrystals can be applied onto the surface of the substrate by any method including spin casting, drop casting, roll coating, drop on demand inkjet printing, PDMS (polydimethylsiloxane) stamp printing, electrostatic layer by layer assembly.

In another aspect, a kit is provided for monitoring and manipulating cellular transmembrane potentials, comprising a substrate and an activation platform, wherein the activation platform is disposed on a surface of the substrate, wherein the activation platform comprises one or more layers of nanocrystals. The substrate included in the kit can be a glass coverslip, a container, a multi-well plate, a ceramic microsphere, or a carbon nanofiber.

The semiconductor nanocrystal-based materials provided herein offer numerous advantages over traditional organic voltage sensitive dyes, since these nanocrystals have large Stokes shift, high quantum yields, photostability, and multiplexing capability. These properties make these materials particularly useful for high throughput drug discovery screening applications. Nanocrystal-based activation platforms are capable of generating light-triggered action potential in excitable cells and can be repeatedly trigger cell activation upon illumination with pulses of light. The activation platform is capable of delivering a physiologically relevant activation stimulus compatible with optical interrogation methods. The activation platforms described herein provide a non-invasive approach for interrogating cells and can be used in both cell-based assays and tissue slices in the absence of any adverse effects on cellular morphology, differentiation and physiological responses. Thus, these platforms are compatible with short-term cell culture for kinetic assays. A further use for the activation platforms described herein is in mixed cultures to study synaptic physiology. By stimulating pre-synaptic cells optically, their post-synaptic partners can be monitored for elicited changes. An important omission in most drug studies of ion channels is that these studies are done in the absence of normal synaptically elicited activity, although all ion channels in normal brains depend on this. Methods are provided herein that allow actual synaptic behavior where fields of synapses can be controlled and monitored optically without the need to penetrate individual neuron pairs with electrodes. These methods can be scaled to fields or networks of cells, which has to date not been practically feasible using traditional approaches. In addition, subcellular domains can be stimulated and monitored, including dendritic abhors, independent of somal activation. The sensing and activation platforms described herein also can be used in in situ, whole brain applications and have therapeutic potential to treat denervated tissues. For example, activation particles delivered in situ can be activated by pulses of light to restore or control neuronal activation in CNS or PNS or heart or muscle tissue. The materials and methods described herein also can be used as an in vivo to investigate and better understand synaptic activity and neuronal physiology in in vivo and in situ models of neurophysiology, including mice, rat, rabbit, cat, monkey, dog, pig and eventually human in clinically validated and justified applications.

DESCRIPTION OF THE FIGURES

The following figures form part of the present specification and are included to further demonstrate certain aspects of the present invention. The invention may be better understood by reference to one or more of these figures in combination with the detailed description of specific embodiments presented herein.

DETAILED DESCRIPTION OF THE INVENTION

Figure 1:
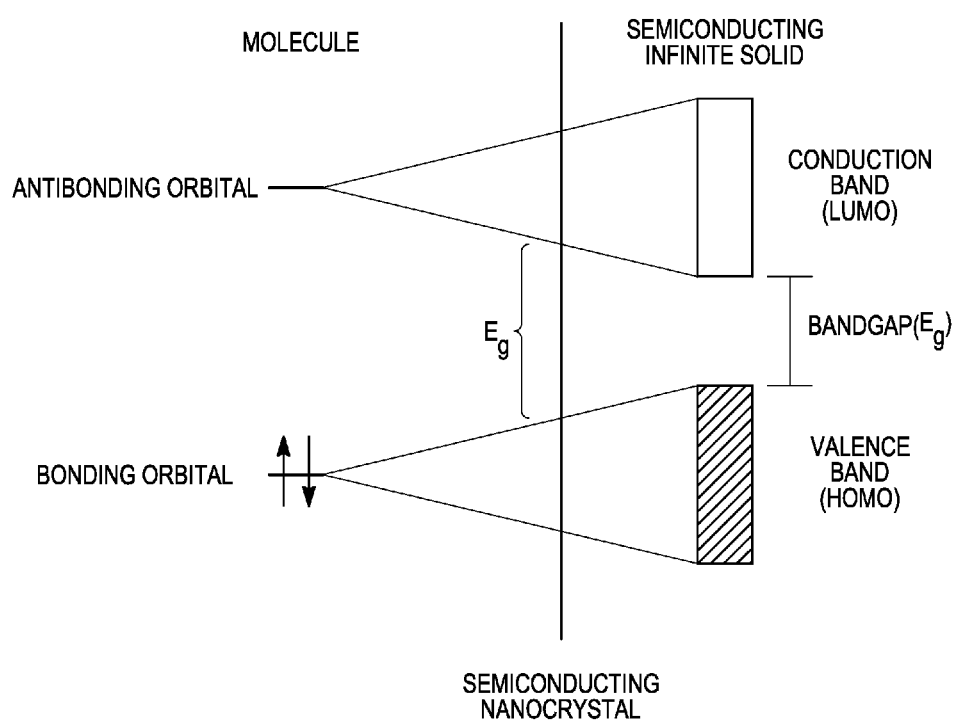
FIG. 1 is a diagram depicting the energy bandgap ($E_g$) of a semiconducting nanocrystal relative to the energy bandgap of a semiconducting infinite solid and the electronic energy levels of a molecule.

Unless defined otherwise, all technical and scientific terms used herein have the same meaning as is commonly understood by one of ordinary skill in the art to which this invention belongs. All patents, applications, published applications and other publications referred to herein are incorporated by reference in their entirety. If a definition set forth in this section is contrary to or otherwise inconsistent with a definition set forth in the patents, applications, published applications and other publications that are herein incorporated by reference, the definition set forth in this section prevails over the definition that is incorporated herein by reference.

As used herein, "a" or "an" means "at least one" or "one or more."

As used herein, the term "about", when used to describe a numerical value, shall encompass a range up to ±15% of that numerical value, unless the context clearly dictates otherwise.

While compositions and methods are described in terms of "comprising" various components or steps (interpreted as meaning "including, but not limited to"), the compositions and methods can also "consist essentially of" or "consist of" the various components and steps, such terminology should be interpreted as defining essentially closed-member groups.

While the visualization of the localization of biologically relevant molecules inside living cells is important, the need for a better understanding of cellular homeostasis in health and disease dictates the necessity to create new materials (e.g., fluorescent probes) and methods that allows tracking of activities in inter and intracellular signaling pathways with spatial and temporal fidelity. Each cell has a resting membrane potential originating from the separation of charges across the phospholipid bilayer. Changes in membrane potential are transmitted into cellular responses for different types of cellular proteins, including voltage-gated ion channels, voltage-dependent phosphotases and GPCRs. They control a vast array of cellular processes, including but not limited to development, differentiation, function of the autonomic, enteric, peripheral and central nervous system, heart beat, blood vessel pressure, sensory function, brain function, muscle contraction, synaptic transmission, cell proliferation, and hormone secretion.

The ability to sense, report, and effect changes in membrane potential is crucial for understanding transmembrane signaling and synaptic activity. Although electrophysiological methods are the gold standard for monitoring cellular electrical activity due to their high information content, optical methods have several advantages over electrophysiological methods. In particular, optical methods offer the benefit of being noninvasive, allowing recording from multiple cells at a time, and can be used to investigate a wide range of cell types, including in tissue slices or intact organs.

Provided herein are materials, methods, and kits for performing assays to sense and stimulate changes in cellular transmembrane potentials. In certain aspects, optical methods are provided to non-invasively manipulate the membrane potential of cells (e.g., neurons). The disclosed methods can be used to control the cell functional activity in a temporally precise and spatially resolved manner. In particular, materials and methods are provided for optical voltage sensing and for light-controlled electrical activation of cells. The described materials and methods are useful in monitoring the dynamic changes in cell membrane potential as well as manipulating the cellular function by changing cell membrane potential. Particular methods make use of a light-controlled external activation platform. The activation platform provides a biocompatible interface for cell activation. When the activation platform is placed in close proximity to a cell and is illuminated by visible light, a cumulative electromagnetic field is generated by excitation of the activation platform. This electromagnetic field modulates the cell membrane potential and is simply controlled by switching the light on and off without perturbing the cells of interest. This non-invasive approach is particularly desirable for investigating certain cell types, such as, e.g., stem cells. Further, the light-controlled activation platform allows for repeated stimulation of cells for seconds, minutes, hours, even days by triggering a physiological relevant activation via an optically induced electric field.

Methods are provided herein for non-invasively inducing the activation of ion channels in cells and tissues (e.g., inducing cells to generate an action potential). Inducing cells to generate an action potential is essential when evaluating new potential drugs that target ion channels or when evaluating new drugs that may, as a side effect, alter ion channel function. In addition, the light-controlled activation platform allows for repeated stimulation of cells by triggering a physiologically relevant activation via an electric field.

The activation platform includes one or more types of materials that can induce changes in local electric field upon irradiation with light. Irradiation of the activation platform can cause the materials making up the platform to generate electric current. The electric current produced can in turn trigger voltage changes in the membranes of cells adjacent to or in the in the vicinity of the activation platform. In certain embodiments, the activation platform provided herein exploits the photoelectronic properties of certain types of nanomaterials (e.g., quantum dots).

Potential applications of the activation platform-based assays described herein include functional studies of voltage-sensitive membrane proteins; studies of communications between cells in dissociated cell culture or tissue slices, including synaptic plasticity; cardiology studies; activation-stimulated cellular expansion and differentiation of stem cells. Additional potential applications of the described technology include activation of synaptic function and in whole brains in treatment of depression, degeneration and other manifestations of diminished or altered brain functions, and in other applications involving stimulation of tissue that are currently under control of electrical stimulation (e.g., muscle dysfunction, such as muscular dystrophy, or in cardiac pacemakers)

In one aspect, a method is provided for assaying or monitoring a change in transmembrane potential, comprised of providing at least one target cell; contacting the target with at least one nanostructure (e.g., activation platform), wherein the nanostructure comprises at least one layer of immobilized nanocrystals covered in whole or in part by an adhesive substrate; stimulating the treated target; assaying emission from the nanostructure, and correlating the emission with the change in transmembrane potential. Certain methods utilize light emissive nanocrystals positioned in the target cell plasma membrane for assaying emission. The nanostructures described herein generally have at least one dimension that is on the nanometer size scale. For example, a nanostructure can be formed of one or more layers of nanocrystals, where the thickness of the nanostructure is about 5-100 nm.

An optional additional step can comprise assaying emission from the nanostructure after the contacting step but before the stimulating step. This additional step can act as a "control" or "blank" measurement.

Due to their unique physical and photochemical properties, semiconductor nanocrystals (e.g., QDOT nanocrystals from Life Technologies Corporation, Carlsbad, Calif.) provide a platform for multiplexed fluorescence-based detection of unparalleled power and simplicity. QDOT nanocrystals are used for bright, photostable and multicolor cell and tissue imaging, flow cytometry, western blotting, single molecule detection, in vivo imaging and more. The methods described herein take advantage of the unique physical and photochemical properties of quantum dots and extend their use beyond these established "light bulb" applications.

In a specific embodiment, multiple layers of nanocrystals are deposited on a solid support such as a coverslip and a single layer of an adhesion substrate (e.g., protein or organic chemical based adhesive) is deposited that covers the nanocrystals. The cells are then contacted with the adhesion substrate covering the nanocrystals or placed on the adhesion substrate for a time suitable to allow attachment. In some embodiments, the cells can attach and/or grow on the coverslip for one day, two days, three days, or five days or more. In certain embodiments, a nanostructure comprising at least one layer of nanoparticles, e.g., nanocrystals, covered by at least one layer of an adhesion substrate forms an activation platform.

Any suitable adhesion substrate can be employed. Adhesion substrates are preferably non-toxic to living cells. In one embodiment, the adhesion substrate is poly-L-lysine. Other attachment or adhesion substrates include those that allow cells to bind the substrate with or without eliciting or inducing morphological changes, differentiation, cellular proliferation, apoptosis, stasis or other physiological changes. Such substrates include, but are not limited to fibronectin, collagens I and IV, or other collagens, elastin, hyaluronic acid, laminin, matrigel, lectins, antibodies to cellular membrane proteins, RGD peptides and their progeny, and the like. Alternatively, the adhesion substrate can include a fluorinated material, such as a sulfonated tetrafluoroethylene based fluoropolymer-copolymer (available under the tradename NAFION from E. I. du Pont de Nemours and Company; Wilmington, Del.). The cells can attach through any mechanism. In some embodiments, only a single layer of adhesive materials is used to cover the layers of nanocrystals. Additional layers may be employed that do not interfere with the energy transfer from the nanocrystals to the attached cells.

The contacting step can comprise contacting the cells with the adhesion substrate layer for any suitable amount of time. In some embodiments, the cells can be stimulated during the contacting step. In some embodiments, stimulatory factors, apoptotic factors, small molecules, antibodies, and the like can be added to the deposited activation layer and/or the media coating the attached cells to influence the signaling environment and assess the effects of changes in membrane potential under particular environmental stimuli. Further examples of stimulation methods include electrical stimulation, magnetic stimulation, chemical stimulation, biological stimulation, or combinations thereof. Examples of electrical stimulation include the use of a patch clamp, and application of an external electric field. Examples of chemical stimulation include contacting the target with a potassium salt or a sodium salt, or with different types of intramembrane pore-forming molecules. Examples of biological stimulation include activating the target with a light-sensitive ion channel, or contacting the target with the chemical entities, acting as modifiers of ion channel activity. Examples of magnetic stimulation include activating the target with alternating electromagnetic field of the appropriate frequency and amplitude.

Targets can be electrically stimulated by a variety of methods. One stimulation protocol (voltage amplitudes and duration of stimulation) is often chosen based on activation kinetics of the ion channel of interest. For example, targets can be maintained at a first membrane potential voltage, subjected to a depolarizing pulse at a second membrane potential voltage, and returned to the first membrane potential voltage. The second membrane potential voltage is typically more positive than the first membrane potential voltage, but it is possible that the first membrane potential voltage is more positive than the second membrane potential voltage. For example, the first membrane potential voltage can be negative, while the second membrane potential voltage can be positive. An example is −70 mV for the first membrane potential voltage, and +40 mV for the second membrane potential voltage. Alternatively, the first or second membrane potential voltage can be 0 mV. Examples include −200 mV for the first membrane potential voltage, and 0 mV for the second membrane potential voltage. An additional example is 0 mV for the first membrane potential voltage, and 200 mV for the second membrane potential voltage. Specific examples of first membrane potential voltages and second membrane potential voltages can be independently selected from about −200 mV, about −180 mV, about −160 mV, about −140 mV, about −120 mV, about −100 mV, about −80 mV, about −60 mV, about −40 mV, about −20 mV, about 0 mV, about 20 mV, about 40 mV, about 60 mV, about 80 mV, about 100 mV, about 120 mV, about 140 mV, about 160 mV, about 180 mV, about 200 mV, and ranges between any two of these values.

Alternatively, more complicated voltage patterns can be used in the methods. The methods can further comprise exposing the targets to at least one step voltage prior to subjecting them to the depolarizing pulse at a second membrane potential voltage. The step voltage is an intermediate voltage between the first membrane potential voltage and the second membrane potential voltage. The step voltage can be used to measure leak subtraction. For example, a first membrane potential voltage of −80 mV, a step voltage of −50 mV, and a second membrane potential voltage of 20 mV can be used.

The depolarizing pulse can generally be applied for any length of time. For example, the depolarizing pulse can be applied for up to about 5,000 seconds. Examples of the length of time include about 10 microseconds, about 1 milliseconds, about 10 milliseconds, about 100 milliseconds, about 1 second, about 2 seconds, about 3 seconds, about 4 seconds, about 5 seconds, about 10 seconds, about 20 seconds, about 30 seconds, about 40 seconds, about 50 seconds, about 60 seconds, about 70 seconds, about 80 seconds, about 90 seconds, about 100 seconds, about 500 seconds, about 1,000 seconds, about 2,000 seconds, about 3,000 seconds, about 4,000 seconds, about 5,000 seconds, and ranges between any two of these values.

The target can be one or more suitable intact cells which have a membrane and membrane potential. Any suitable cell can be employed including, but not limited to bacterial (Gram-positive or Gram-negative), eukaryotic, prokaryotic, fungal, insect, avian, reptilian, oocyte, fly, zebrafish, nematode, fish, amphibian, or mammalian cells. Examples of primary mammalian cells include human, mouse, rat, dog, cat, bear, moose, cow, horse, pig, or Chinese hamster ovary ("CHO") cells. Other examples of types of cells include immune system cells (e.g., B-cells, T-cells), oocytes, red blood cells, white blood cells, neurons, epithelial, glia, fibroblast, cancer cells, and immortalized cells.

Nanostructures can take various configurations. For example, nanostructures can be in the form of nanoparticles (e.g., nanocrystals), nanowires, films, patterned substrates, and meshes. An exemplary nanostructure is a nanowire formed of a semiconductor material (e.g., CdSe) that can induce or report a change in electrical potential. For example, a nanowire can be inserted through or immediately adjacent to a cell membrane, a field of cells or synaptic neuropil or a muscle cell or other excitable cell. The nanowire can act can act in a manner analogous to a standard electrical stimulating electrode, such as a pacemaker electrode. A change in the membrane potential of the cell is created by the nanowire and triggers a field potential and action potentials in the surrounding tissue.

In certain embodiments, the nanostructure is an activation platform formed from one or more layers of support material (e.g., nanocrystals). In other embodiments, the nanostructure comprises activation particles (e.g., spheroids) that can placed deep into excitable tissue and accessed with excitation light. Methods of creating nanostructures or activation platforms comprising layers of nanoparticles (e.g., nanocrystals) covered by at least one layer of adhesion substrate include the immobilization of the nanocrystal layers onto the supportive structures (for example, onto the bottom of a well in the microtiter plate), covered with at least one layer of adhesion substrate, and subsequent addition of solution containing cells to an experimental chamber (such as a microtiter plate well). Any combination of nanoparticles (e.g., nanocrystals) can be employed in building the activation platform. A single type of nanoparticle can be employed or a mixture of nanoparticles differing in properties of interest may be employed.

Nanoparticles can generally be any suitable semiconductor nanocrystals or quantum dots. Quantum dots are nanometer-scale inorganic crystals containing from a few hundred to a few thousand atoms of a semiconductor material. Their behavior is governed by the laws of quantum physics. Quantum dots are not quite a molecule, although they have discreet electronic energy levels, and not a bulk semiconductor either, although they demonstrate spin-orbit coupling and have large dielectric constants. A small semiconducting nanocrystal behaves more like a molecule and therefore has a higher bandgap energy, while a large semiconducting nanocrystal behaves more like an infinite solid and therefore has a lower bandgap energy. The differences between the electronic properties of a semiconductor nanocrystal, a molecule, and semiconducting infinite solid are depicted in FIG. 1.

Figure 2:
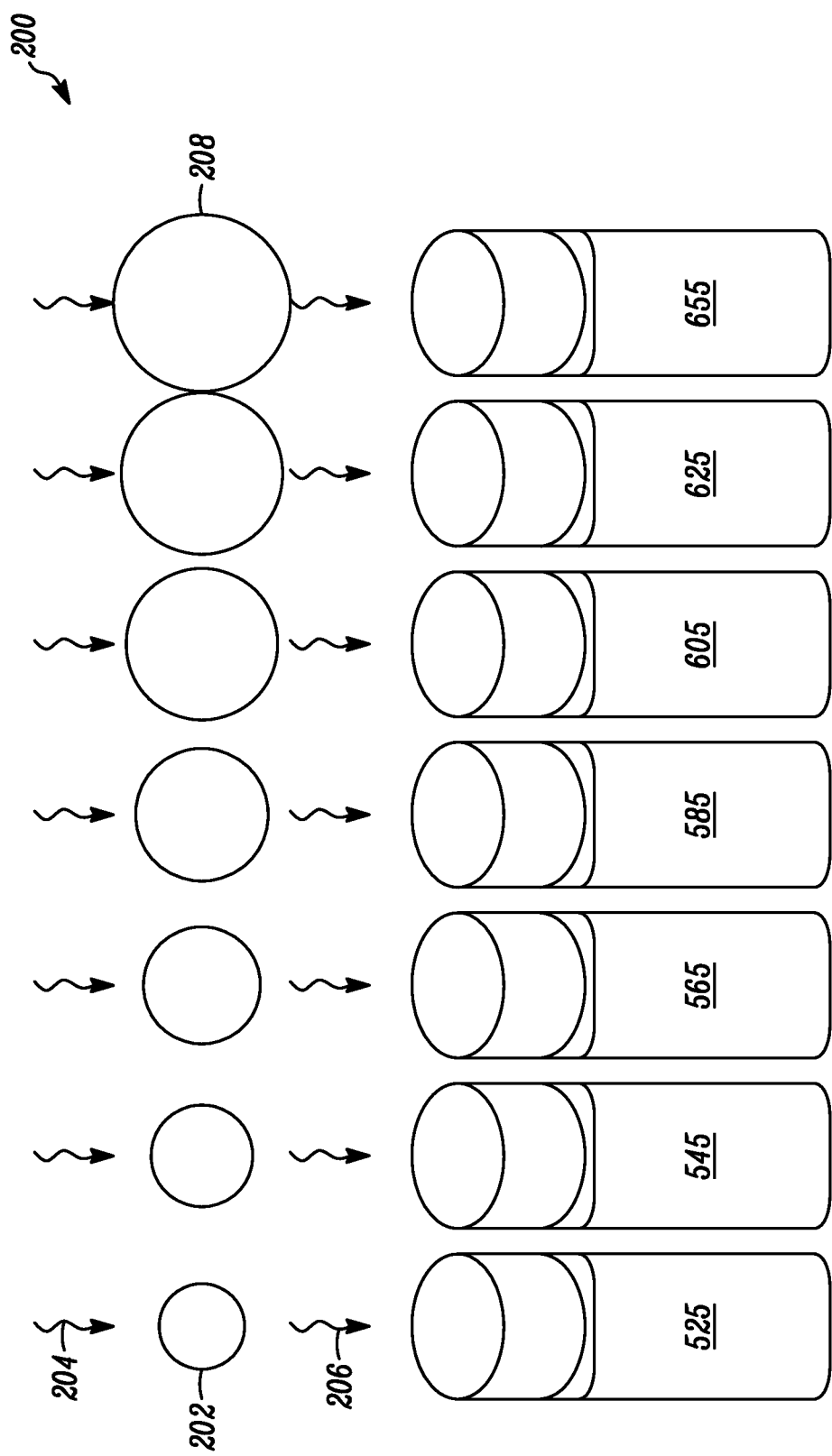
FIG. 2 is a diagram showing the correlation between the size of semiconductor nanocrystals and their emission wavelength due to the size-dependent energy bandgap for semiconductor nanocrystals.
Figure 3:
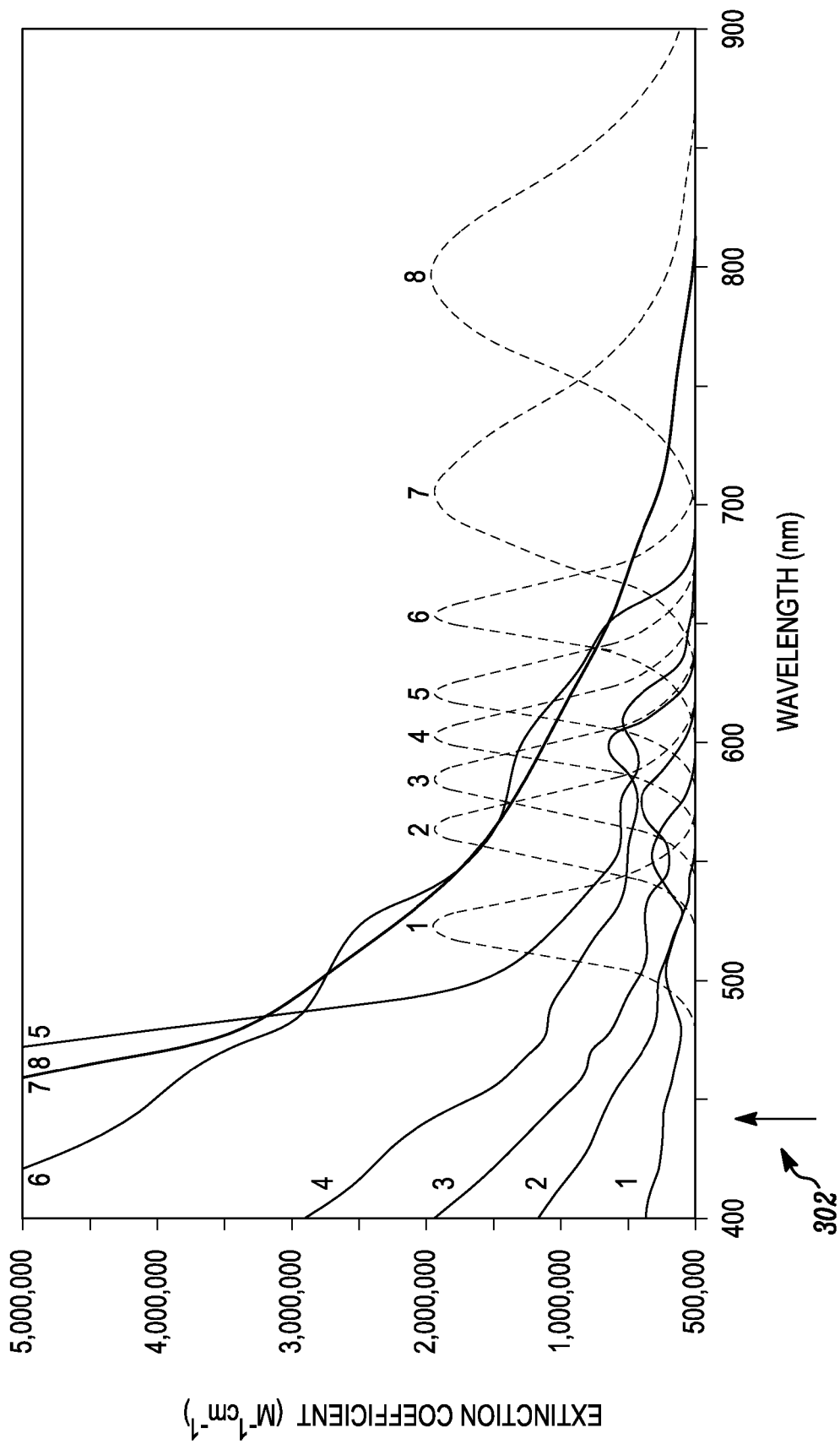
FIG. 3 is a plot showing the optical properties of differently-sized quantum dot nanocrystal conjugates: QDOT 525 (1), QDOT 565 (2), QDOT 585 (3), QDOT 605 (4), QDOT 625 (5), QDOT 655 (6), QDOT 705 (7), QDOT 800 (8). The quantum dot materials exhibit broadband absorption (solid lines) upon excitation with violet light and exhibit emission over a broad range of wavelengths. The size of the quantum dot material dictates its emission spectra (dashed lines).

Quantum effects become increasingly important as the physical size of a structure is reduced. The quantum confinement of light-generated excitons in three spatial dimensions determines the photophysical properties of quantum dots, such as the effective bandgap of the nanocrystals and hence the wavelength of fluorescence. Quantum dots fluoresce differently than traditional fluorophores. Absorption of any photons with energies higher than the bandgap causes the formation of excitons, or Coulomb-correlated electron-hole pairs. This broadband absorption spectrum means that quantum dots absorb light at every wavelength to the blue of their emission and many colors can be obtained by exciting quantum dots of different sizes at a single wavelength to the blue of the bluest emission. Electrons and holes stay separated for tens to hundreds nanoseconds and then radiatively recombine leading to the emission of a photon. FIG. 2 shows a series of vials 200 where each vial contains a population of quantum dots of differing size and illustrates that quantum dots emit light at a wavelength (e.g., 525 nm to 655 nm) that depends on their size. Referring to FIG. 2, illumination of a smaller sized quantum dot 202 with light 204 results in emission of light 206 at shorter wavelength (e.g., 525 nm), whereas larger sizes of quantum dots 208 emit at longer wavelength (e.g., 655 nm). Quantum dot materials can exhibit broadband absorption upon excitation with light having a wavelength of, e.g., about 400-475 nm, and can emit light spanning a broad range of wavelengths (FIG. 3). Referring to FIG. 3, excitation of quantum dots of varying size at about 430-450 nm (shown with arrow 302) results in emission of light at wavelengths ranging from about 500 to about 900 nm, depending on the size of the quantum dot. Further, the emission spectra of quantum dots are extremely narrow and symmetric.

Quantum dots are composed of hundreds to thousands of repeating atoms, each contributing to the nanocrystal's ability to absorb light. Consequently, quantum dots have exceptionally high extinction ($10^6$-$10^7$ $M^{-1}$ $cm^{-1}$), far greater than any organic dye. Moreover, optimally synthesized quantum dots possess quantum yields that approach the theoretical maximum of 100%. This combination of extraordinary absorption properties with the large quantum yields results in materials that are more than a thousand times brighter and more sensitive than organic fluorophores, often leading to a dramatic reduction of the working concentration for biological applications and drastically heightened ability to detect rare events. Additionally, the high photostability of quantum dots enables long-term imaging experiments under conditions that would cause the photo-induced deterioration of other types of fluorophores. Quantum dots are transforming life science imaging due to their extraordinary photostability, brightness, broad excitation, narrow emission, long fluorescence lifetimes, and multiplexing capability.

Quantum dots are highly engineered materials that typically contain several structurally distinct elements. Semiconductor nanocrystals typically have a semiconductor core, a shell, and optionally, one or more surface treatments. Exemplary nanocrystals include, but are limited to those described in U.S. Pat. Nos. 5,505,928; 5,990,479; 6,114,038; 6,207,229; 6,207,392; 6,251,303; 6,319,426; 6,444,143; 6,274,323; 6,306,610; 6,322,901; 6,326,144; 6,423,551; 6,699,723; 6,426,513; 6,500,622; 6,548,168; 6,576,291; 6,649,138; 6,815,064; 6,819,692; 6,821,337; 6,921,496; 7,138,098; 7,068,898; 7,079,241; and 7,108,915. The nanocrystal core largely determines its critical light absorption and emission characteristics. Nanocrystal cores have been broadly studied and improvements in synthesis have led to the optimization of key physiochemical properties resulting in nanocrystal cores with uniform size distributions and intense, narrow emission bands following photo-excitation. However, nanocrystal cores alone lack sufficiently intense or stable emission intensities for most applications. Nanocrystal cores are particularly sensitive to their environment; for example, the aqueous environment required for many biological applications can lead to the complete destruction of the luminescence of nanocrystal cores. Thus, methods to photostabilize nanocrystal cores (e.g., protect their luminescent properties) and make them stable and useful in aqueous media are of great interest for biological applications. Commonly, this is achieved by applying a shell over the core, to form a so-called core/shell nanocrystal.

The ability to coat nanocrystal cores has been an area of much research, and coating nanocrystal cores with an inorganic shell to form "core/shell nanocrystals", has resulted in improved emission intensity, chemical and photochemical stability, reduced self-quenching characteristics, stability in a variety of environments, and the like. The impact of coating nanocrystal cores with an inorganic shell on underlying luminescence energies is not well understood and is generally controlled based on a small set of criteria such as, for example, the choice of the coating material and the density and thickness of the shell.

The inorganic shell is generally thought to passivate the outermost surface of a core nanocrystal thereby reducing or eliminating the surface energy states associated with the core and insulating the core from the outside environment. This can reduce or eliminate the nonradiative loss of excitons from the core to the environment, preserving the efficient fluorescence properties that a core can possess. Photochemical degradation may also be reduced, and emission efficiency and stability may be improved, by coating a core with an inorganic shell.

Figure 4A:
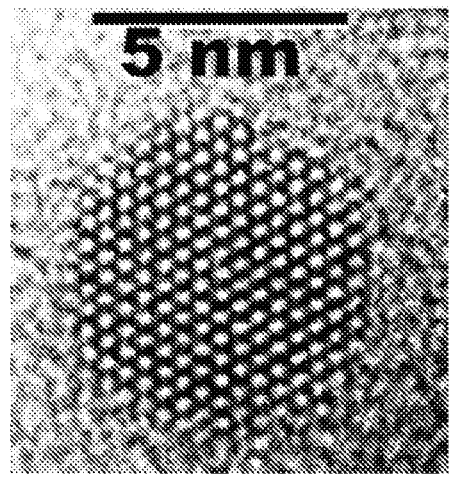
FIG. 4 shows crystal structures for a single CdSe quantum dot having a cross-sectional diameter of about 5 nm (A) and an assembly of uniformly-sized quantum dots (B)
Figure 4B:
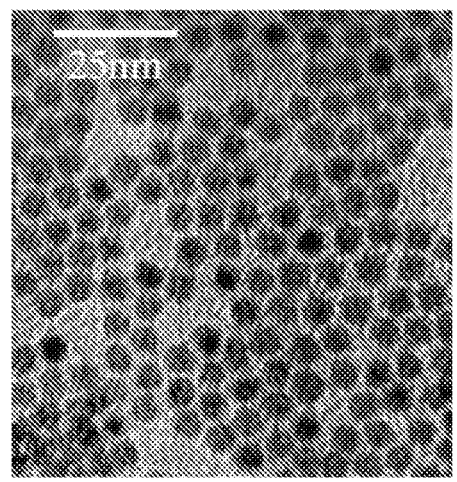

While a nanoparticle core determines its color, a nanoparticle shell determines its brightness, photostability and environmental insensitivity. The shell material is usually chosen according to the electronic properties that are insulating to the core. The choice of shell material is generally made to match the core material. For example, the shell material may generally have a wider band gap than the core, which enables it to protect the activated state that the core occupies when it has been photoactivated, forming a separated electron and hole. The shell may ideally be chosen to have an atomic spacing and lattice structure that closely match those of the core material to best preserve the photophysical attributes of the core, since irregularities in the interface between core and shell may be responsible for non-radiative energy dissipation mechanisms that reduce luminescent efficiency. Proper deposition of an inorganic shell to these quantum dot cores results in a composite core-shell structure with significantly enhanced chemical and photophysical properties. The most common quantum dots are composed of CdSe and exhibit emission wavelength maxima that can vary from ~400 nm to ~650 nm as the size of the nanocrystals is varied from 2-7 nm. FIG. 4 shows crystal structures of typical quantum dots at different levels of detail.

Figure 5:
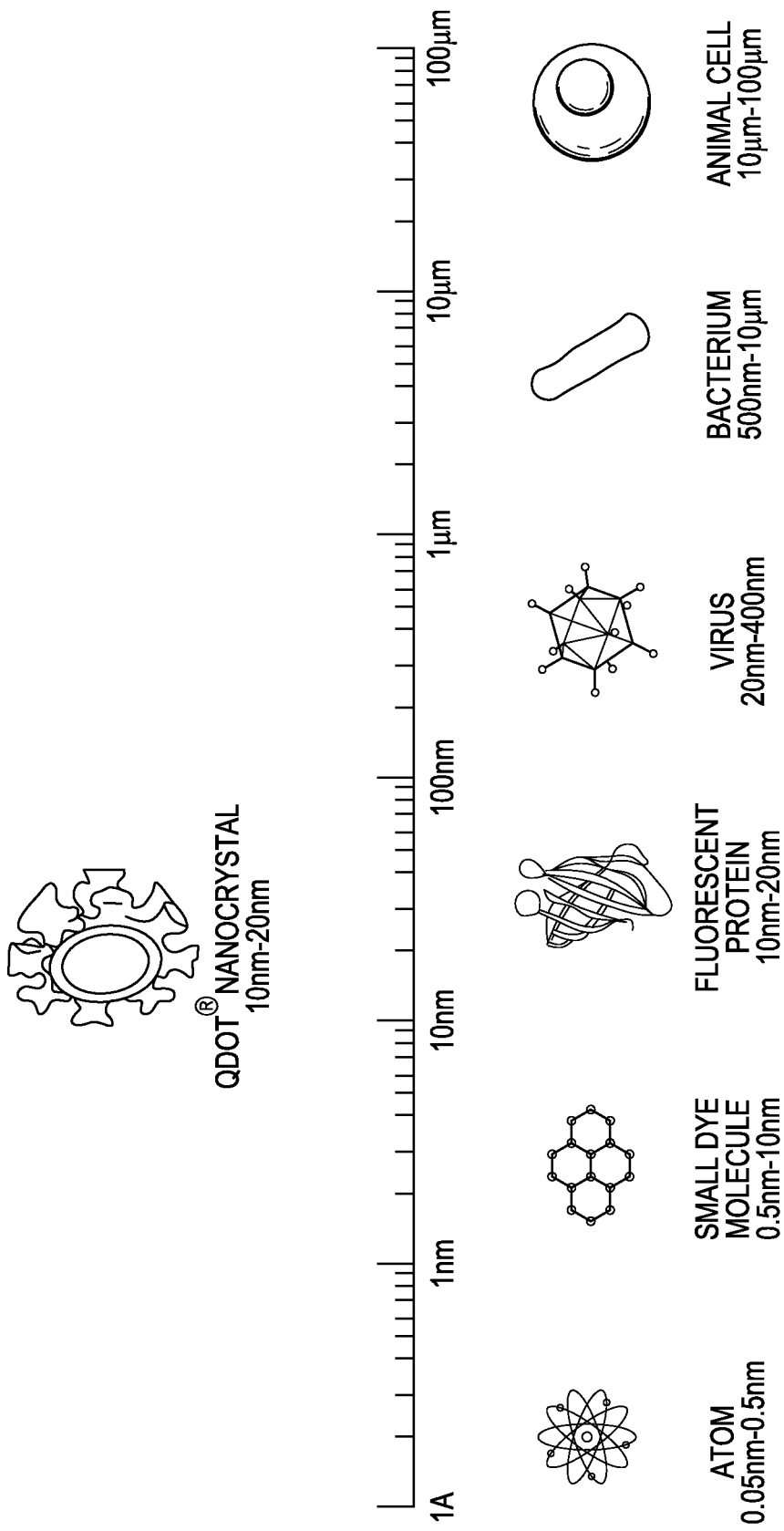
FIG. 5 is a plot showing the relative size of quantum dot nanocrystals.

To be useful in most fluorescence-based biological applications, bare core-shell nanocrystals typically need to be modified via attachment of a ligand to the surface of the shell to become dispersible in water and reactive toward bio-functional modifications. The resulting nanoparticles can have the size of about 10-20 nm, similar to green fluorescent proteins (GFPs) (FIG. 5). The fully-assembled quantum dots are insensitive to the external environment, and, therefore, are useful as quantitative as reagents for macromolecule detection.

The semiconductor nanocrystal core and shell can independently be made of a material of an element from Group 2 or 12 of the Periodic Table of the Elements, and an element or a combination of elements selected from Group 16 of the Periodic Table of the Elements. Examples of such materials include ZnS, ZnSe, ZnTe, CdS, CdSe, CdTe, HgS, HgSe, HgTe, MgS, MgSe, MgTe, CaS, CaSe, CaTe, SrS, SrSe, SrTe, BaS, BaSe, and BaTe. Alternatively, the semiconductor nanocrystal core and shell can independently be made of a material made of an element from Group 13 of the Periodic Table of the Elements, and an element from Group 15 of the Periodic Table of the Elements. Examples of such materials include GaN, GaP, GaAs, GaSb, InN, InP, InAs, and InSb. Alternatively, the semiconductor nanocrystal core and shell can independently be made of a material made of an element from Group 14 of the Periodic Table of the Elements. Examples of such a material include Ge, and Si. Alternatively, the semiconductor nanocrystal core and shell can independently be made of lead materials such as PbS or PbSe. The semiconductor nanocrystal core and shell can be made of alloys or mixtures of any of the above listed materials as well.

The semiconductor nanocrystal can generally be of any size (average diameter), but typically are about 0.1 nm to 1,000 nm in size. More narrow ranges of sizes include about 0.1 nm to about 1 nm, about 1 nm to about 50 nm, and about 1 nm to about 20 nm. Specific size examples include about 0.1 nm, about 0.5 nm, about 1 nm, about 2 nm, about 3 nm, about 4 nm, about 5 nm, about 6 nm, about 7 nm, about 8 nm, about 9 nm, about 10 nm, about 11 nm, about 12 nm, about 13 nm, about 14 nm, about 15 nm, about 16 nm, about 17 nm, about 18 nm, about 19 nm, about 20 nm, about 25 nm, about 30 nm, about 35 nm, about 40 nm, about 45 nm, about 50 nm, and ranges between any two of these values. In certain embodiments, semiconductor nanocrystals having an average diameter of about 1 to about 20 nm have been found to be particularly practical. Other embodiments utilize nanocrystals having an average diameter of about 3 to about 10 nm.

A typical single-color preparation of nanocrystals has crystals that are preferably of substantially identical size and shape. Nanocrystals are typically thought of as being spherical or nearly spherical in shape, but can actually be any shape. Alternatively, the nanocrystals can be non-spherical in shape. For example, the nanocrystal's shape can change towards oblate spheroids and rods for redder colors. It is preferred that at least about 60%, at least about 70%, at least about 80%, at least about 90%, at least about 95%, and ideally about 100% of the particles are of the same size. Size deviation can be measured as root mean square ("rms") of the diameter, with less than about 10% root mean square being preferred. Size deviation can be less than about 10% rms, less than about 9% rms, less than about 8% rms, less than about 7% rms, less than about 6% rms, less than about 5% rms, or ranges between any two of these values. Such a collection of particles is sometimes referred to as being "monodisperse".

It is well known that the color (emitted light) of the semiconductor nanocrystal can be "tuned" by varying the size and composition of the nanocrystal. As discussed above, nanocrystals preferably absorb a wide spectrum of wavelengths, and emit a narrow wavelength of light (see, FIG. 3). The excitation and emission wavelengths are typically different, and non-overlapping. The width of emission is preferably less than about 50 nm, and more preferably less than about 20 nm at full width at half maximum of the emission band (FWHM). Examples of emission widths (FWHM) include about 50 nm, about 40 nm, about 30 nm, about 20 nm, and about 10 nm. The emitted light preferably has a symmetrical emission of wavelengths. The emission maxima can generally be at any wavelength from about 200 nm to about 2,000 nm Examples of emission maxima include about 200 nm, about 400 nm, about 600 nm, about 800 nm, about 1,000 nm, about 1,200 nm, about 1,400 nm, about 1,600 nm, about 1,800 nm, about 2,000 nm, and ranges between any two of these values.

Nanocrystals can also have a metal core, and in some cases, a surrounding shell structure. The metal core can be made from noble metals. Examples of such metals include silver, gold, and copper.

Optionally, an organic or other overcoat that is selected to provide compatibility with a dispersion medium may be applied to the shell on part or most of its surface; this overcoat is useful to adapt the inorganic particle to be soluble in or readily dispersed in a medium of choice, which may be aqueous or organic, hydrophilic or hydrophobic. For certain applications, the nanocrystals can have surface coatings adding various functionalities. For examples, nanocrystals can be derivatized to improve water solubility or to provide reactive groups for attachment to biomolecules. For example, the nanocrystals can be coated with lipids, phospholipids, fatty acids, polynucleic acids, polyethylene glycol, primary antibodies, secondary antibodies, antibody fragments, protein or nucleic acid based aptamers, biotin, streptavidin, proteins, peptides, small organic molecules, organic or inorganic dyes, precious or noble metal clusters.

Alternatively, the nanocrystals can be made from a range of inorganic materials, including silicon, alumina, zirconia, ceria, yttria and oxides of tin and zinc. For example, silicon nanoparticles possess many of the advantageous features of compound semiconductor nanocrystals, such as size-tunable luminescence across the visible spectrum. In addition, silicon nanoparticles also low toxicity, high biocompatibility, efficient and stable surface functionalization, and potential low cost.

The use of nanocrystals in ion channel assays has multiple desirable features. Since nanoparticles have rapid response times and signal change compared to existing organic, voltage-sensing fluorophores, they are ideal for characterizing action potentials and synaptic activity. The nanocrystals also possess other desirable qualities such as low toxicity, high photo-stability, the ability to be used in multiplexing applications, and their ability to be targeted using conjugated or otherwise associated materials. Further, in contrast to organic fluorophores that can create toxic reactive species (e.g., singlet oxygen) as they photobleach, nanocrystals have not been shown to produce any such toxic species. Due to their high photo-stability, fast response times, large signal change and low toxicity, nanocrystals are ideal materials for use in the study of ion channels and neuronal function in living cells.

Spectral characteristics of nanocrystals can generally be monitored using any suitable light-measuring or light-accumulating instrumentation. Examples of such instrumentation are CCD (charge-coupled device) cameras, video devices, CIT imaging, digital cameras mounted on a fluorescent microscope, photomultipliers, fluorometers and luminometers, microscopes of various configurations, and even the human eye. The emission can be monitored continuously or at one or more discrete time points. The photostability and sensitivity of nanocrystals allow recording of changes in electrical potential over extended periods of time.

Additional methods of assaying the emission from the nanostructure include measuring changes in light intensity, light polarization, light absorption, color of the emission, emission lifetime or half-life, or the "blinking" pattern.

Various materials are described herein that are useful for monitoring changes and/or manipulating electrical potential at or in cellular membranes. Certain materials can be used as voltage sensors (e.g., as an alternative to fluorescent indicator dyes). Such materials are capable of sensing changes in electrical potential, where the change is detected as a change in the material's optical properties (e.g., wavelength and/or intensity). Other materials are capable of effecting or modulating changes in cellular electrical potentials. For example, upon illumination with light, nanocrystals become a path for free charge carrier flow through the membrane, passing an electric current and in turn affecting the transmembrane potential. This way, voltage control over the cell could be achieved by changing, for example, the incident light's intensity and/or polarization.

Materials are provided herein that can be localized in/at the cell membranes, either permanently or temporary. The ability of nanocrystals to be retained in or at a cell membrane can be a function of core, shell, and/or coating compositions and/or configuration, as well as changes in particle shape.

Nanoparticles can be synthesized in shapes of different complexity such as spheres, rods, discs, triangles, nanorings, nanoshells, tetrapods, and so on. Each of these geometries has distinctive properties: spatial distribution of the surface charge, orientation dependence of polarization of the incident light wave, and spatial extent of the electric field.

In order to manipulate free charge carrier concentration and mobility, nanoparticles can be doped with impurities such as indium, phosphorus, boron, and aluminum, and so on. A blend of nanoparticles and organic polymers may be advantageous for this application as nanoparticles are highly efficient in conducting electrons, whereas polymers are better at conducting holes. Functionalization of semiconductor nanoparticles with chromophores could also optimize this application by separating photon absorption from free charge carrier transport.

The duration that a particular sensor can remain in/at a membrane is often dictated by the coating used to treat the particle surface. Representative coatings include peptides that are capable of associating with the plasma membrane, antimicrobial peptides such as gramicidin, melittin and alamethicin, and a helical amphipathic and pore-forming peptides. Peptides can be immobilized onto quantum dots using methods known to those skilled in the art, such as coupling a histidine residue in a peptide to the surface of a quantum dot whose surface has been treated with imidazoles. Certain embodiments utilize cell penetrating peptides (CPP) that are able to penetrate into cells. Other types of coatings include histidine, lysine, thioglycerol, amphotericin, and cholesterol. A representative coating material for quantum dots includes a positively charged polymer such as polyethylenimine (PEI). PEI polymers are hydrophilic and have an affinity toward metal ions, making this class of polymers particularly useful for forming stable complexes with quantum dots. PEI polymers can be used to form coatings on quantum dots that can render the quantum dots water dispersable and water-stable, without compromising quantum efficiency. Further, PEI polymers include an abundance of amine functionalities that can be crosslinked using, for example, bifunctional amine reactive compounds.

The conditions suitable for interaction or insertion can include a variety of methods. Examples of such methods include passive or active uptake via endocytosis, electroporation, liposome-mediated delivery, pluronic block copolymer-mediated delivery, cell-penetrating peptide-mediated uptake, protein-mediated uptake, microinjection, transfection, viral delivery, optoporation, pore-forming substrates, membrane intercalators, or combinations thereof.

As nanoparticles are approximately the same thickness as a cellular membrane, insertion into the membrane exposes the poles of the nanoparticle to both the extra- and intracellular space. Upon illumination with light, nanoparticles become a path for free charge carrier flow through the membrane, passing an electric current and in turn affecting the transmembrane potential. This way, voltage control over the cell could be achieved by changing, for example, the incident light's intensity and/or polarization.

Accordingly, methods for the optical control of the transmembrane potential of a target can comprise providing at least one target, wherein the target is a cell or cellular fraction; contacting the target with at least one nanostructure under conditions suitable for interaction or insertion of the nanostructure with a cellular or subcellular membrane to prepare a treated target; delivering energy to the treated target; and detecting response of the target.

The cells can be any of the cells described above. The nanostructure can be any nanostructure including any of the nanostructures described above.

An additional embodiment provided herein is directed towards the use of an activation platform to control and/or manipulate the transmembrane potential of cells. Nanoparticles (e.g., nanocrystals) exposed to light can act as a generator of a local electromagnetic field in their vicinity. The effect is believed to be due to creation of free charge carriers (electron-hole pairs upon illumination of nanoparticles) and consecutive charge separation. Without wishing to be bound by theory, the currently proposed mechanism of action is electrostatic coupling of the cellular membrane and the surface of semiconductor, effectively forming a capacitor. When nanocrystals are placed in close proximity to a cell, the cumulative electromagnetic field generated by photo-excited nanocrystals can interact with the cellular transmembrane electrical gradient, resulting in an electromagnetic field that dictates the cellular membrane potential. Local depolarization of part of cellular membrane may be sufficient to generate depolarization in the whole cell.

Accordingly, provided herein is a method for the optical control and/or manipulation of the transmembrane potential of a target cell comprising at least one target cell; contacting the target cell with an activation platform under conditions suitable for attachment of the target cell to the activation platform to form a treated target; delivering energy to the treated target through the activation platform; and detecting response of the target.

The delivering energy can include delivering light, electrical energy, magnetic energy, and so on. The delivering energy step can be performed by essentially any illumination method, including laser illumination, mercury lamp illumination, xenon lamp illumination, halogen lamp illumination, LED illumination, and so on. An illuminating step is preferably performed at a wavelength or wavelength range suitable for absorption by the nanocrystals in the activation platform.

The detecting step can be performed using a variety of methods using any suitable light-measuring or light-accumulating instrumentation. Examples of such instrumentation are a camera, a digital camera, a video camera, a CMOS camera, a CCD camera, a digital camera mounted on a fluorescent microscope, a photomultiplier, a fluorometer, a luminometer, a microscope, and even the human eye. The cellular response can be monitored continuously or at one or more discrete time points in any suitable manner.

Alternatively, the detecting step can include use of a secondary detection mechanism. An example of such a secondary detection mechanism is the use of fluorescence resonance energy transfer ("FRET"). With FRET, the nanostructure can transfer its energy to a second molecule that then emits a detectable signal. Additional secondary detection mechanisms rely on changes in a cell that can be independently detected. For example, the cell may undergo lysis. Alternatively, the cell may undergo a chemical change, increasing or decreasing the concentration of one or more chemical or biochemical agents (e.g., calcium ions) that can be independently measured.

At least one additional material can be added to at least one cell or to the treated cell to assay the cellular response to the additional material. For example, the cell can be first contacted with the at least one nanocrystal, illuminated, and the cellular response detected as a "control" sample. The treated cell can then be contacted with the additional material to prepare a material-treated cell, illuminated, and detected. This second cellular response can be compared with the first (control) cellular response. A difference between the first cellular response and the second cellular response would indicate whether the addition of the material had any effect on cellular behavior. A different additional material or an additional dose of the same additional material can be added, followed by illumination and detection of a third cellular response. This can be done in a serial manner any number of times. For example, increasing dosages of a material can be detected, resulting in a third cellular response, a fourth cellular response, a fifth cellular response, a sixth cellular response, and so on. These serial cellular responses can be plotted or otherwise compared, and the effects of the serial treatments can be determined.

Alternatively, "control" and "test" samples can be performed in parallel. For example, a first cell can be contacted with a nanocrystal, illuminated, and the control cellular response detected. In parallel, either serially or simultaneously, a second cell can be contacted with a nanocrystal and a test material, illuminated, and the test cellular response detected. The control cellular response and the test cellular response can be compared.

The at least one additional material can generally be any material. Materials known to modulate ion channel behavior can be employed in combination with the activation platform. See, e.g., Ashley (ed.), ION CHANNELS: A PRACTICAL APPROACH (Oxford University Press 1996). Examples of such materials include drug candidates, modulators of cellular function, molecular moieties for enhanced drug delivery, molecular probes candidates, and so on.

In addition to use of the above described nanocrystals, modified nanocrystals can be used to achieve a strong, stable, and controllable local electric field. Such modifications include high surface charge (e.g., CdTe/CdSe as core/shell combination), doping nanocrystals with materials that can act as donors or acceptors of one type of free charge carriers, creating nanocrystals with p- or n-type surface traps, conjugation of molecules that would contribute to a charge separation, and so on. Active generation of a cellular transmembrane potential can be achieved through use of nanocrystals that can convert light into electric power.

In certain embodiments, the semiconductor nanocrystal includes a material of an element from Group 12 (IIB) of the Periodic Table of the Elements, and an element or a combination of elements selected from Group 16 (VIA) of the Periodic Table of the Elements. For example, the nanocrystal core can be formed of CdSe, CdTe, CdS, or HgTe, or a mixture or alloy of thereof. Alternatively, the nanocrystal core can include a material of an element from Group 13 and an element of a combination of elements selected from Group 15 For example, the nanocrystal core can be formed of InP or a mixture or alloy thereof.

Semiconductor nanocrystal materials are often constructed to improve their optical properties. Such materials typically include a semiconductive core surrounded by an insulating shell material, which can often be relatively thick (e.g., about 2 nm to about 4 nm). The presence of the insulating shell, however, can render nanocrystals relatively insensitive to their local environment. Certain applications, in contrast, require that the nanocrystal materials be especially sensitive to changes in local electrical field. Sensitivity can be enhanced by altering the composition and/or configuration of the shell material. Nanocrystal materials are provided herein that can sense or modulate changes in local electrical field. These materials are particularly useful in biological assays involving monitoring of voltage-gated ion channels. Accordingly, a semiconductor nanocrystal is provided that includes a shell layer covering only a portion of the semiconductor core. Certain nanocrystals include a shell material that is thin enough to permit the flow of electrons through the activation platform, while still enhancing the particle's optical properties. For example, the shell is relatively thin (in comparison to commercially available quantum dots) and includes only several monolayers of passivating shell materials. For example, one type of environmentally-sensitive nanocrystal includes a core formed of CdSe and/or CdTe surrounded by a thin ZnS or CdS shell.

Additional types of nanocrystals are provided that are engineered to not fluoresce in the presence of an electrical field. Such materials are designed to efficiently convert light to electrical current and can be useful in applications involving non-optical detection of changes in electrical current. For such applications, semiconductor nanocrystals are provided that do not to include an insulating shell. Nanocrystals absent a shell can effectively absorb light to produce and conduct electrical current. When in the form of an activation platform, as described herein, electrical current can freely travel through the platform and effectively depolarize cells in contact with the platform. Particles consisting only of a semiconductor core (and no shell), with or without additional surface coatings, can be excited optically and detected in a non-optical manner, such as with a patch pipette, without a loss in depolarization efficiency.

Nanocrystals can be modified with surface coatings to add various functionalities or to impart alter the properties of the underlying nanocrystal. In addition to the surface coatings already described, other types of ligands and coating materials can provide additional benefits for photovoltaic applications. For example, nanocrystals can be treated to make them more water-soluble or water-dispersible. Nanocrystals are typically synthesized in the presence of hydrophobic solvents such as TOPO and TOP that render the nanocrystal water-insoluble. The water-solubility of the nanocrystals can be enhanced by derivatization with hydrophilic and/or charged ligands. For example, nanocrystals can be subjected to a ligand exchange reaction to exchange surface-bound hydrophobic groups with more hydrophilic ligands. In some embodiments, the nanocrystal can be coated with a ligand or polymer that imparts a net positive charge or a net negative charge to the nanocrystal. Representative examples of materials that can be used to produce nanocrystals having a net negative charge include those containing, e.g., one or more thiol, sulfonate, or carboxylate groups, such as 1-thioglycerol, thioglycolic acid, 2-mercaptoethane sulfonate, poly (acrylic acid) or a derivative thereof, or lipoic acid. Representative examples of materials that can be used to produce nanocrystals having a net positive charge include, e.g., polyethylenimine (PEI), cysteamine, polyallylamine, histidine, polyhistidine, lysine, and polylysine.

Alternatively, or in addition, nanocrystals can be coated or derivatized with a compound (e.g., polymer) containing reactive functional groups (e.g., polymerizable groups). Upon appropriate activation (e.g., light or heat), the reactive functional groups can polymerize to form a coated nanocrystal. Representative examples of polymers having reactive or polymerizable groups that can be used to form a polymer layer on the nanocrystal surface include vinyl polymers and acrylic polymers.

Other examples of materials that can be used to coat or cover the nanomaterials (e.g., as a coating on the nanocrystal or as a layer in the activation platform) described herein include naturally occurring or synthetically prepared polymeric materials. Representative examples of naturally-occurring polymeric materials include agarose, and various cell adhesion materials, such as, poly-L-lysine, poly-D-lysine, poly L- and D-ornithin, fibronectin, RGD peptides, matri-gel, collagens I and IV, lectins, elastin, hyaluronic acid, laminin, antibodies to cell surface proteins, extracellular proteins and the like. One representative example of a synthetically prepared polymer is poly(diallyldimethylammonium chloride) (PDDA). Certain activation platforms utilize PDDA in one or more layers of the assembly.

An activation platform for use in the described methods includes one or more types of nanomaterials (e.g., nanocrystals) described herein. The activation platforms can have a variety of configurations, depending on the particular nanomaterial used and application. For example, activation platforms can be substantially planar and can take the form of, e.g., a film, an array, a patterned coating, or the like, or can have a more complex, three-dimensional configuration. A three-dimensional structure may be engineered by altering various design parameters such as, for example, the number of nanocrystal layers, composition (e.g. CdSe, CdTe, CdS, ZnSe, ZnS, or the like) of the nanoparticles, and the type and/or size of nanoparticles in different layers.

The activation platform is typically immobilized on a substrate or surface. For use in optical assays, it is desirable that the substrate be optically clear such that it does not significantly impede or scatter the light used in the assay (e.g., light having a wavelength in the near UV to the near IR). Certain embodiments require that the substrate be made of an optically clear (e.g., transparent) material, such as glass or plastic.

Substrates can have various configurations. For example, the substrate can be a planar surface or a curved surface, Representative examples of substrates include, microscope slides, coverslips, test tubes, containers, multiwell plates (e.g., microtiter plates), micro-beads (glass or polymer), ceramic microspheres, carbon nanofibers, and the like.

In certain embodiments, the activation platform further includes one or more layers of an adhesion substrate (e.g., adhesion layer). As mentioned above, the adhesion substrate allows cells to bind the substrate with or without eliciting or inducing morphological changes, differentiation, cellular proliferation, apoptosis, stasis or other physiological changes. Adhesion substrates are preferably non-toxic to living cells and non-insulating materials that do no impede the activation response. Examples of materials for preparation of the adhesion substrate include, for example, poly-L-lysine, poly-D-lysine, fibronectin, collagen, elastin, hyaluronic acid, laminin, extracellular matrix protein, fluorinated surfactants, poly l- and d-ornithin fibronectin, RGD peptides, matri-gel, collagens I and IV, lectins, elastin, hyaluronic acid, laminin, antibodies to cell surface proteins, extracellular proteins and the like.

The type and arrangement of nanoparticles is typically selected to maximize transmission of charge from the activation platform into the cell and to minimize conduction of charge within the activation platform. In certain embodiments, this can be achieved by designing the activation platform in the form of a film. Such a film can be constructed so as to be highly insulating. Although charge does not move far within a highly insulating material, is does move by a certain distance. In some embodiments, the conductivity of the film is such that the distance the charge travels is on the same size scale as the film thickness. This distance is typically much smaller than the diameter of a cell (diameter of a cell in on the micrometer size scale) so charge does not move around the cell. The film can include one or more types of nanomaterials (e.g., nanocrystal particles) and can be formed of one or more layers of material. In addition, the nanoparticles often include a surface coating or treatment that prevents or minimizes leaching of the particles into the aqueous medium. The nanoparticles can be dispersed homogeneously throughout the film layer(s) or can be localized in specific domains of the film and can be embedded into the film and/or disposed on the surface of the film. For example, the nanoparticles can be arranged in discrete domains within the film or on the surface of a film to form a one- or two-dimensional array. Alternatively, the nanoparticles are arranged adjacently in a "shoulder-to-shoulder" fashion on a substrate surface. In yet another system, the activation platform is in the form of a patterned array. Such arrays can be formed, for example, of discrete patches (e.g., spots) of nanocrystal materials. The spacing between patches is selected such as to eliminate conduction of electrons between the films. In some systems, the patches are about the size of a cell. Cell-sized patches can be formed of a highly conductive material, while being able to direct all charge toward the cell.

Figure 15:
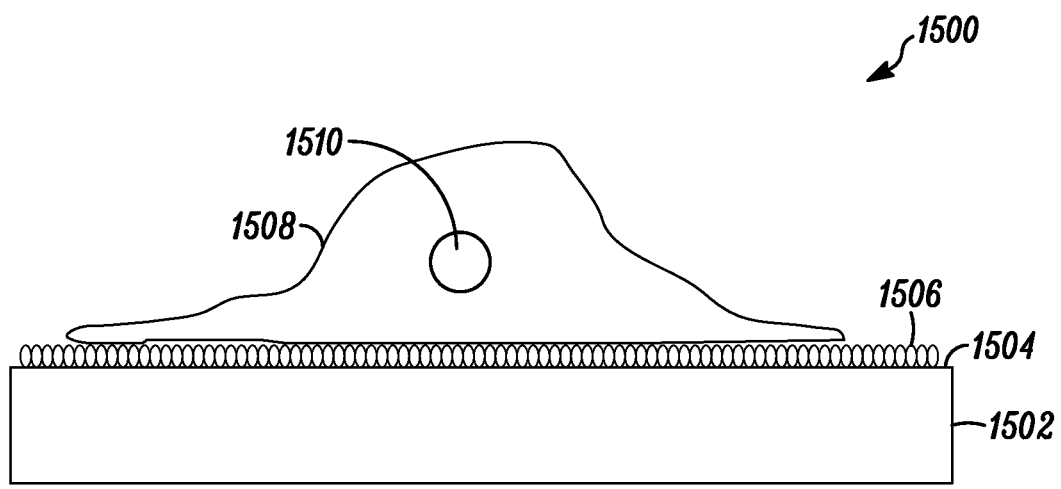
FIG. 15 is a schematic presentation of a quantum dot nanocrystal-based activation coverslip showing the interface between nanomaterials and live cells.
Figure 15A:
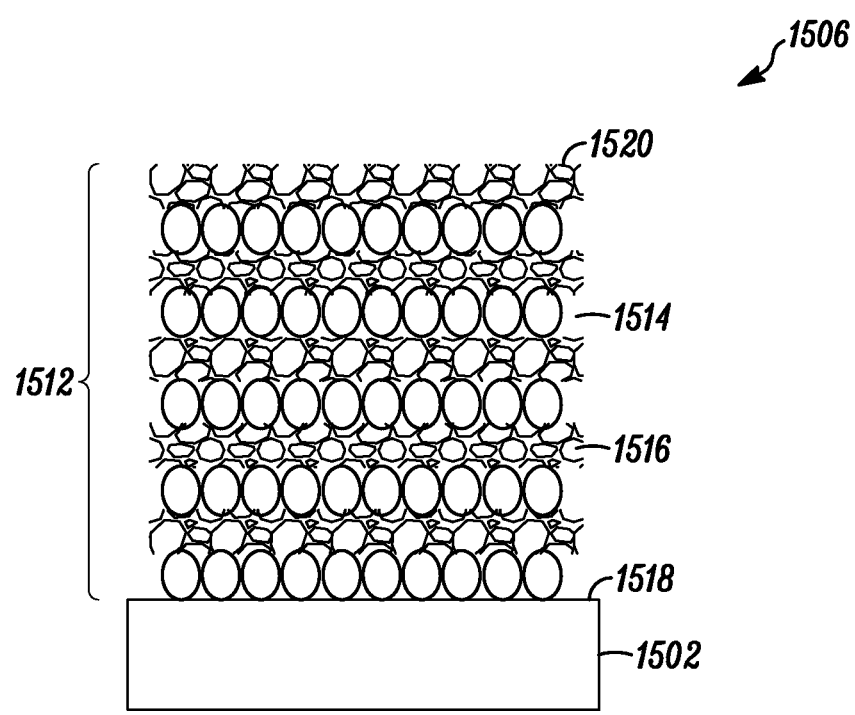
FIG. 15A is an expanded view of the activation platform disposed on a coverslip.

Certain films are saturated with nanocrystal particles. Films containing high concentrations of nanocrystals allow nanocrystals to closely pack and can efficiently carry current and depolarize cells. The film should not be toxic to the cells and can be of any thickness that does not impede depolarization of the cell. For example, films can range in thickness from about 10 nm to about 100 nm. Certain films are highly uniform and can be prepared by providing a uniform concentration of nanocrystal particles across the entire surface of the film and/or have a uniform thickness Films can be formed of multiple nanocrystal layers (e.g., prepared by layer-by-layer assembly (LBL)). An exemplary activation platform is depicted in FIG. 15. Referring to FIG. 15, an assay system 1500 includes a substrate 1502 (e.g., a glass coverslip) having immobilized on its surface 1504 an activation platform 1506 onto which is deposited a cell 1508 with a resting potential (e.g., −70 mV) containing a nucleus 1510. In a specific embodiment shown in FIG. 15A, activation platform 1506 includes multiple layers 1512 of quantum dots 1514. Activation platforms can include positively and/or negatively charged quantum dots. In some activation platforms, alternating layers of positively and negatively charged quantum dots are used. The number of quantum dot layers used is dictated by various factors, such as by the type of nanocrystals used, the configuration of substrate, the type of cell to be assayed, the time available to prepare the film, the type of cell adhesion layer used, the surface coating of the nanocrystal, whether the film is patterned or not and the type of polymers used but typically ranges from about 1 to about 30 layers. Certain activation platforms use films having less than 20 layers or less, or about 2 to about 15 layers. Other activation platforms have 10 or less layers, or about 5 to about 10 layers. Particular activation platform use only about 5-7 layers. Each nanocrystal layer can include the same type of material. Alternatively, different layers can include different types of nanocrystals of nanocrystals of differing charge. Optionally, one or more layers of a material 1516 (e.g., a polymer) is interposed between adjacent quantum dot layers. One type of polymer that can be used in this manner is PDDA. In certain types of activation platforms, a material 1516 (e.g., a polymer) is disposed on a surface 1518 of substrate 1502 to immobilize the activation platform 1506 on the substrate. Optionally, an adhesion substrate (e.g., an adhesion layer) 1520 covers the stack of quantum dot layers 1512 to enhance adhesion of the cell 1508 to the adhesion substrate 1506. The adhesion layer composition generally is selected to achieve close contact between cells and adhesion substrate.

Another type of activation platform includes a plurality of quantum dot layers immobilized on a substrate formed of or coated with a transparent conductor, such as indium tin oxide (ITO). Such substrates can be treated with quantum dot layers directly. Alternatively, such substrates can reside on all or a portion (e.g., in the form of a patterned array) of an optically transparent substrate, such as a glass microscope slide. The activation platform includes a plurality of layers, where each layer includes a population of quantum dots. The population typically comprises quantum dots having a uniform size. The layers and types of quantum dots are arranged so as to facilitate flow of electrons through the activation platform, such as to activate a cell on or in the vicinity of a surface of the activation platform. The activation platform can be excited by irradiation at a wavelength specific to a particular type of quantum dot in the construct. The following exemplary activation platform illustrates one particular configuration that can be used in the methods described herein. Such a platform includes a planar ITO substrate that has immobilized on one surface a first layer of nanocrystals that absorb red wavelengths of light and a second layers of nanocrystals that absorbs blue wavelengths of light, but not red. Successive layers (e.g., third and fourth layers) of nanocrystals can be added to the construct which absorb, for example, green and yellow light, respectively. Because the energy of the conduction band for quantum dots can be tuned by particle size, electron transfer can be optimized by optimizing the size of the particles in each successive layer. For example, the platform can include a first layer of CdTe nanocrystals having an emission wavelength of about 700 nm. The construct includes a second layer of CdSe nanocrystals having an emission wavelength of about 490 nm, a third layer of CdSe nanocrystals having an emission wavelength of about 545 nm, and a fourth layer of CdSe nanocrystals having an emission wavelength of about 630 nm. An optional cell adhesion layer may be deposited on the surface of the fourth layer exposed to the cell (e.g., cell culture medium). An organic semiconductor such as poly(ethylenedioxythiophene) (PEDOT) can be deposited between the ITO substrate and CdTe nanoparticle film to further improve the film efficiency, if required. In this exemplary device, only the CdTe particles can be excited when illuminated with red light. Upon excitation of the CdTe layer, electrons can move from layer to layer to the surface of the activation platform, where they can ultimately modulate the cell's membrane potential.

An additional embodiment provided herein is directed towards one or more containers having a layer of nanostructures or activation platforms deposited on one or more surfaces. For example, the container can be a test tube, centrifuge tube, or microtiter plate (e.g., 96 or 384 well plate). The entire inner surface of the tube or plate's wells can be coated with the nanostructures mentioned above. Alternatively, the lower or bottom inner surface of the tube or wells can be coated with the nanostructures. These assay materials can be stored for subsequent use with cells.

The nanostructures described herein can be constructed using a variety of methods. One representative method for forming an activation platform use layer-by-layer (LBL) assembly. The LBL method includes immersing a charged substrate, for instance negatively charged glass, in a solution of positively charged polyelectrolyte. After rinsing with water, the polyelectrolyte forms a positively charged monolayer on the surface of the substrate. Immersion in a solution of negatively charged nanocrystals forms a new layer, thereby switching the surface charge. This makes possible the adsorption of a new layer of polyelectrolyte. This cycle can be repeated as many times as desired. Finally, one or more layers of an adhesion layer can be deposited to cover the film construct.

Another representative method for preparing an activation platform includes depositing a composition containing a plurality of nanoparticles onto a solid substrate (e.g., a glass coverslip) to form a film. The composition can include a polymer (e.g., agarose, polymethyl methacylate, polyacrylamide, or the like) and optionally solvents, initiators, or other components. The composition can be deposited onto the substrate using any appropriate deposition method known to those skilled in the art including, for example, spin casting, spray coating, drop casting, roll coating, draw coating, drop on demand inkjet printing, PDMS (polydimethylsiloxane) stamp printing, electrostatic layer by layer assembly. Once deposited onto the substrate, the composition can take the form of a film having embedded into it a plurality of nanoparticles. If desired, additional layers of nanoparticles can be deposited onto the substrate using any suitable deposition methods to generate a multi-layered construction. The film can be additionally heated, air-dried, or crosslinked to cure the film and/or remove residual solvent. In certain embodiments, one or more layers of a cell adhesion layer can added on top of the film construct to enhance cell adhesion and viability.

Other representative methods involve drop-casting or spin-coating water-insoluble nanoparticles (e.g., quantum dots) in organic solution onto a substrate. Alternatively, water-insoluble nanoparticles can be dispersed in a volatile organic solvent and sprayed onto the substrate. In any of the methods described herein, an amphiphilic polymer can be deposited onto the nanoparticle film. If solvent is used, deposition of amphiphilic polymer occurs after evaporating the solvent. A cell adhesion layer can added on top of the amphiphilic polymer to enhance cell adhesion and viability.

Also provided herein are kits for conducting assays for the optical sensing, control and/or manipulation of the transmembrane potential of a target cell. Kits can include an activation platform, as described herein, and can include one or more additional components, such as buffers, dyes, primary neurons, growth factors, cell culture media, other cellular and subcellular markers. Certain kits include one or more ion sensitive or voltage-sensitive dyes). For example, kits can include one or more fluorescent calcium, sodium, potassium, ROS, RNS, peroxidation, or pH sensors. In some embodiments, the activation platform is immobilized on a solid support, such as the surface of a container (e.g., a test tube, centrifuge tube, or multiwell microtiter plate) or planar substrate (e.g., a glass microscope slide). Other types of substrates include conductive ceramic materials with activation particles inside and adhesion molecules covering them, or other manifestations of electrodes for temporary and chronic implants in tissue, such as cardiac pacemakers, fine spike-like multiarrays for multi-site penetration into tissues, and others currently under study for brain stimulation.

The following examples are included to demonstrate preferred embodiments of the invention. It should be appreciated by those of skill in the art that the techniques disclosed in the examples which follow represent techniques discovered by the inventor(s) to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the scope of the invention.

EXAMPLES

Example 1

Membrane Labeling with Quantum Dots

Figure 6A:
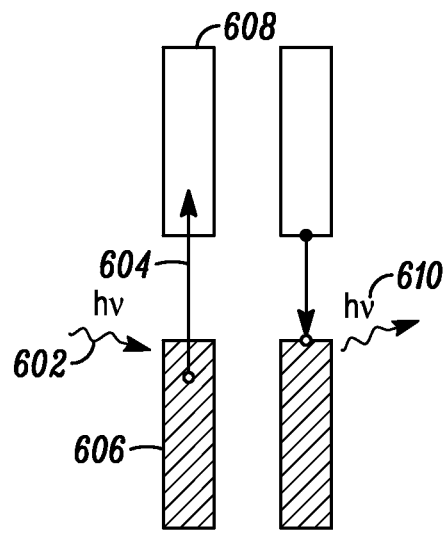
FIG. 6 shows the proposed mechanism of action for a quantum dot nanocrystal-based voltage sensor in the absence (A) and presence (B) of an electric field.
Figure 6B:
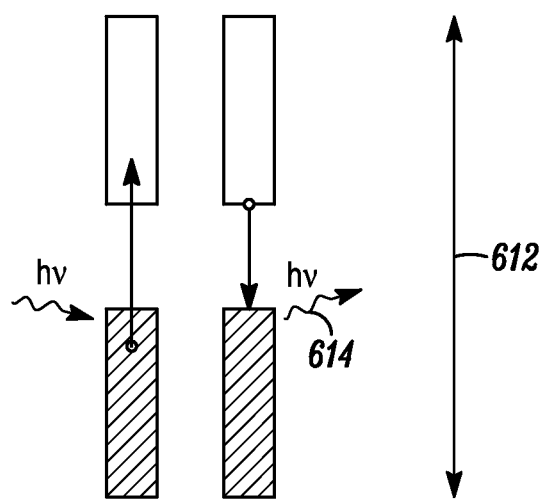

Quantum dots are ideal candidates for use as voltage-sensitive probes, as their physical size is comparable with the thickness of the cell membrane, and their electronic properties make them potentially tunable to the external electromagnetic field. Referring to FIG. 6A, the absorption of a photon 602 having a first wavelength and with energy higher than the band gap 604 between the HOMO valence band 606 and the LUMO conduction band 608 of a quantum dot forms electron-hole pairs than can radiatively recombine to emit a photon 610 having a second wavelength. An intense local electric field (e.g., due to a change in the membrane potential across the lipid bilayer of a cell) can interact with the free charge carriers generated by excited quantum dots. FIG. 6B illustrates schematically how an electrical field 612 can modulate the optical properties of the emitted light 614. For example, a membrane potential of 100 mV across the hydrophobic lipid bilayer translates into an intense local electric field reaching $10^7$ V/m. This large field can interact with free charge carriers (electrons and holes) generated in quantum dots during illumination, leading to modulation of their optoelectronic properties (e.g., changes in intensity and wavelength of emitted light). Referring again to FIG. 6B, the optoelectronic properties of light 614 will be different than those of light 610 in the presence of an electric field 612.

Figure 7A:
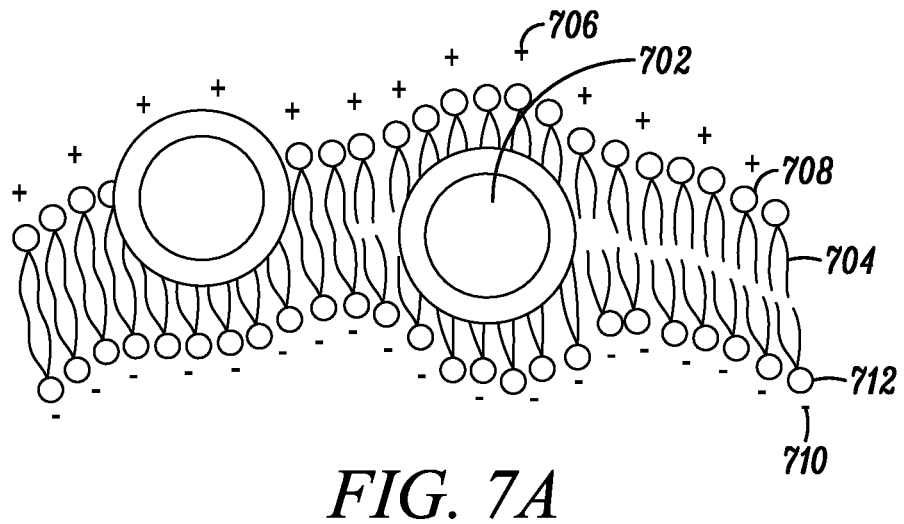
FIG. 7 shows phospholipid cell membranes containing quantum dot nanocrystal-based voltage sensors before (A) and after (B) depolarization of the cell.
Figure 7B:
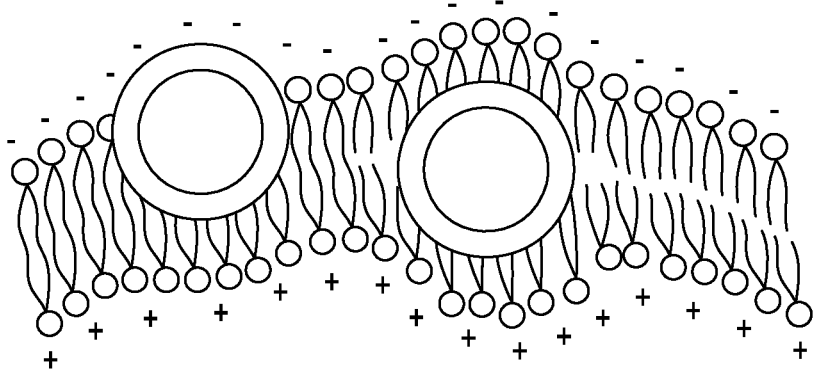
Figure 8A:
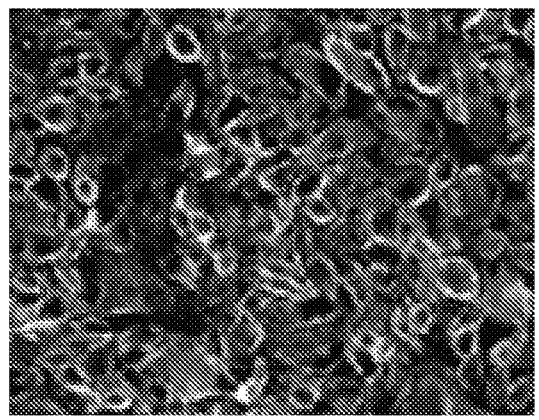
FIG. 8 shows fluorescent images specific membrane labeling of CHO cells (A), NG108 cells (B), and a neuronal network (C) using quantum dot nanocrystal-based voltage sensors.
Figure 8B:
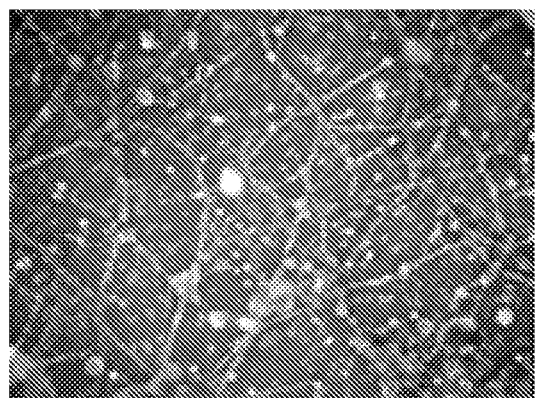
Figure 8C:
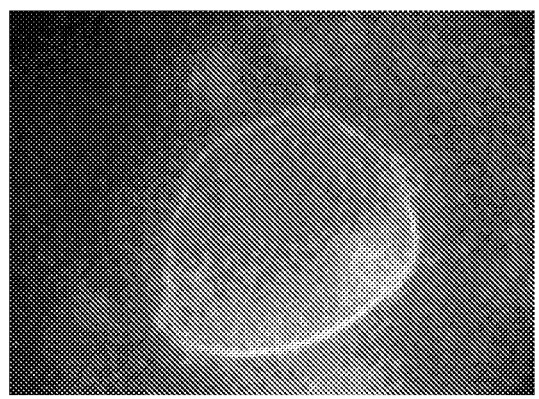

As discussed above, commercially available QDOT nanocrystals have been engineered to maximize environmental insensitivity and typically will not suffice for voltage sensing applications. For use as efficient voltage-sensors and/or activators, the structure of nanoparticles must be engineered in such a way that changes in the electric field will be transduced into changes in quantum dot emission. Options for achieving this sensitivity include changes in the absorption efficiency, exciton behavior, or modulation of an emitted photon. In addition, to sense membrane potential changes with maximal efficiency, quantum dots must be localized in or very near the cell membrane, typically within the highest transmembrane electrical field gradient. Referring to FIG. 7A, a nanoparticle 702 is positioned within a phospholipid cell membrane 704 of a resting cell that has a net positive charge 706 outside the cell (shown as side 708) and a net negative charge 710 inside the cell (shown as side 712). FIG. 7B depicts the reversal of charge on phospholipid cell membrane 704 upon depolarization of the cell. To ensure the intramembrane positioning of a nanoparticle, materials are provided herein that include a specialized coating, such as polyethylenimine (PEI). Coated nanocrystals were positioned within membranes of various cell types. FIG. 8 shows CHO cells (A), NG108 cells (B) and a neuronal network (C) having membranes labeled with one type of quantum dot.

Example 2

Screening Assays of Quantum Dots

QDOT nanocrystal-based optical voltage sensors are provided to monitor rapid changes in cell membrane potential. When localized inside the cellular membrane, the nanoparticles are sensitive to and detect changes in transmembrane voltage gradient and report it as the change in their emission properties. A series of quantum-dots were prepared and screened to monitor their optical properties in response to chemical and electrical stimulation of cells.

A. Effect of Chemical Stimulation

The effect of chemical stimulation on cells treated with quantum dots was monitored according to the following protocol. Cells were incubated with nanocrystal-based voltage sensors in 96-well plates for 1 hour, and then any excess nanoparticles were washed away. A population of labeled cells was depolarized using a chemical stimulus (100 mM KCl), appropriate for high-content imaging experiments.

Figure 10:
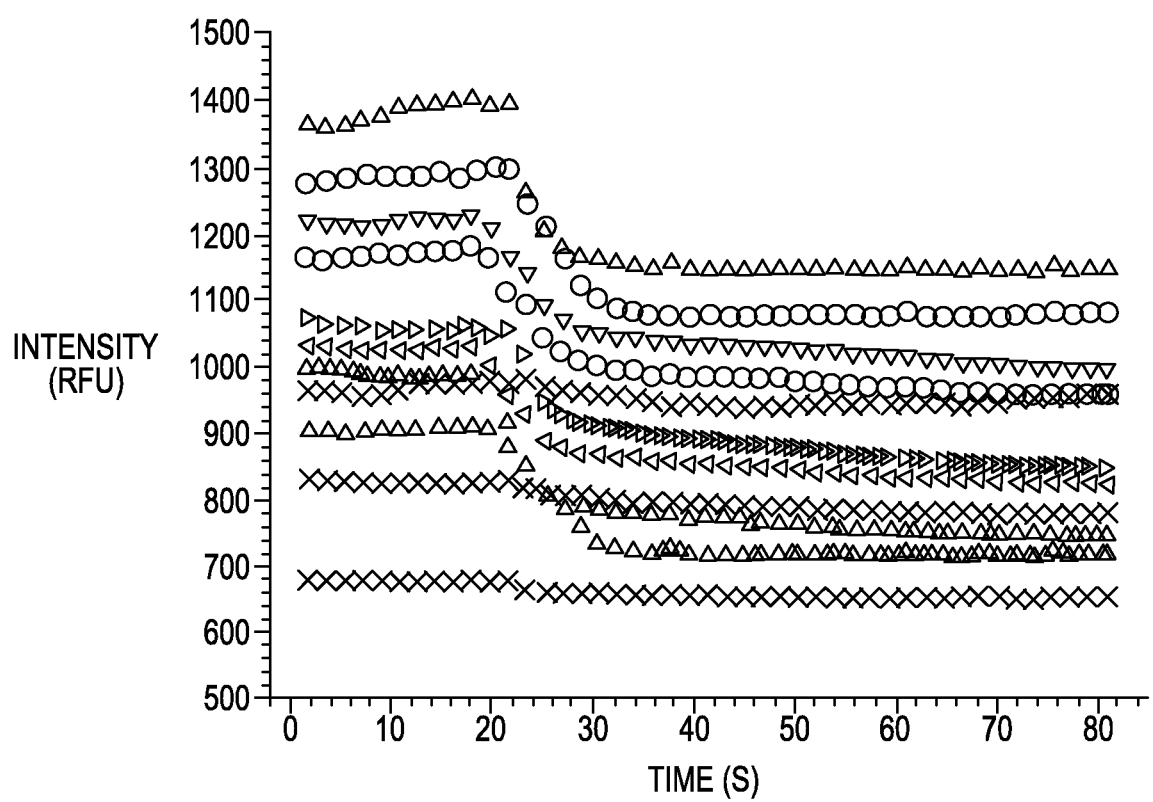
FIG. 10 is a plot showing changes in fluorescent intensity (RFU) over time of one type of quantum dot nanocrystal-based voltage sensors in multiple CHO cells in response to induced membrane depolarization (100 mM KCl application).
Figure 11:
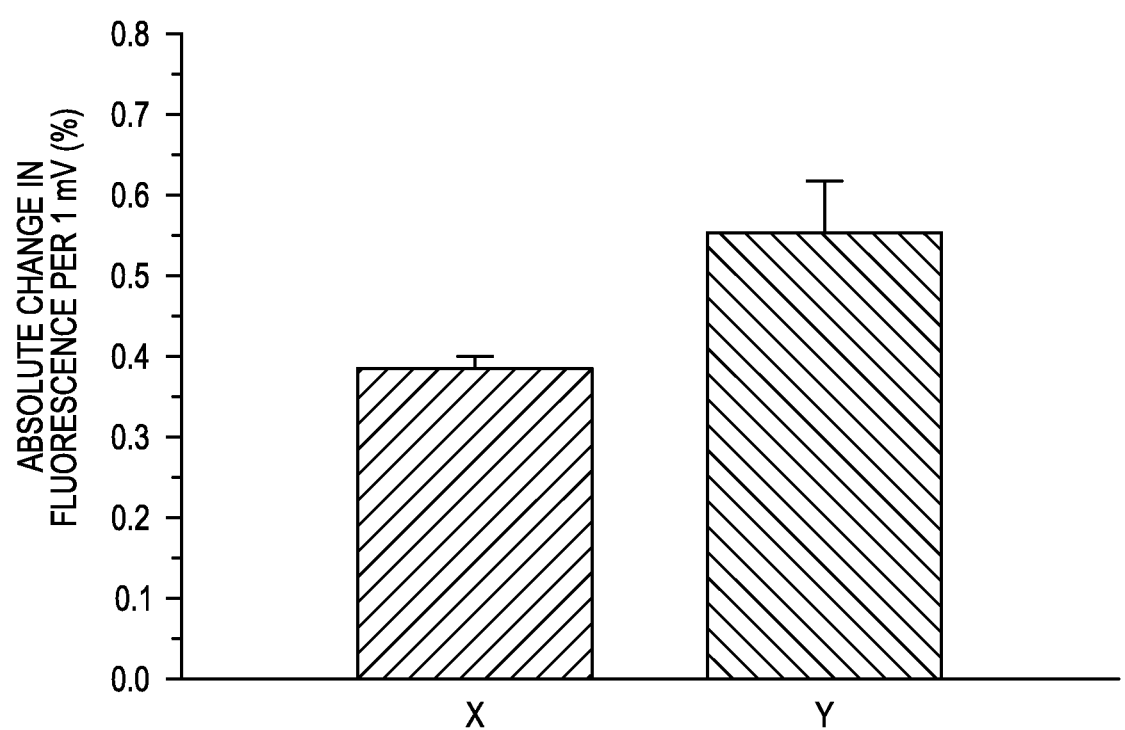
FIG. 11 is a bar graph showing the average fluorescence change for two types (labeled X and Y) of nanocrystal-based voltage sensors.

FIG. 10 shows the emission intensity (expressed as relative fluorescent intensity, RFU) over time for a series of cells labeled with identical core-shell quantum dots (functionalized with PEI). Two different types of PEI coated, core-shell quantum dots (identified as X and Y in FIG. 11) exhibited ~50% fluorescence change per 100 mV in the fluorescence intensity in response to a depolarizing stimulus.

B. Patch Clamp Assay

Figure 9:
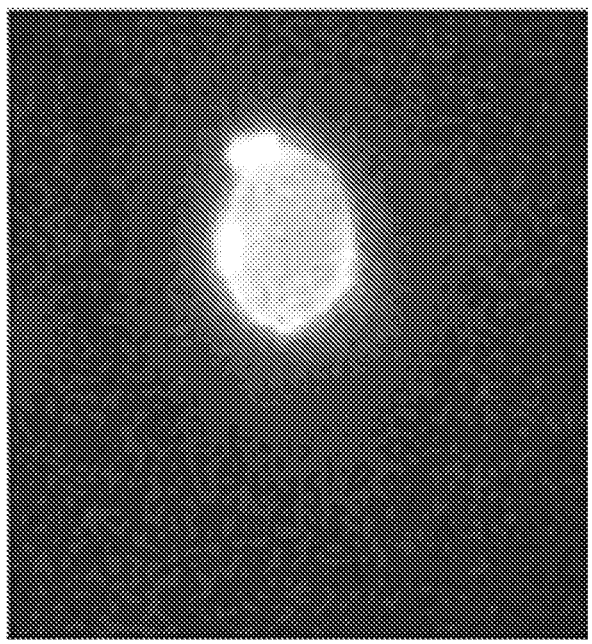
FIG. 9 is a fluorescent image of a CHO cell labeled with a quantum dot-based voltage sensor showing the resting emission intensity.
Figure 12:
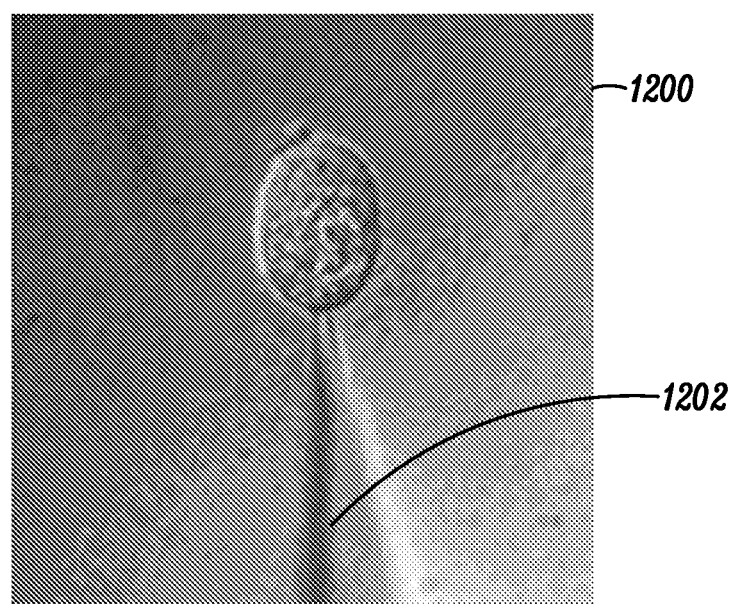
FIG. 12 shows the same CHO cell shown in FIG. 9 labeled with a quantum dot-based voltage sensor prior to being electrically stimulated with a giga seal patch electrode.
Figure 13A:
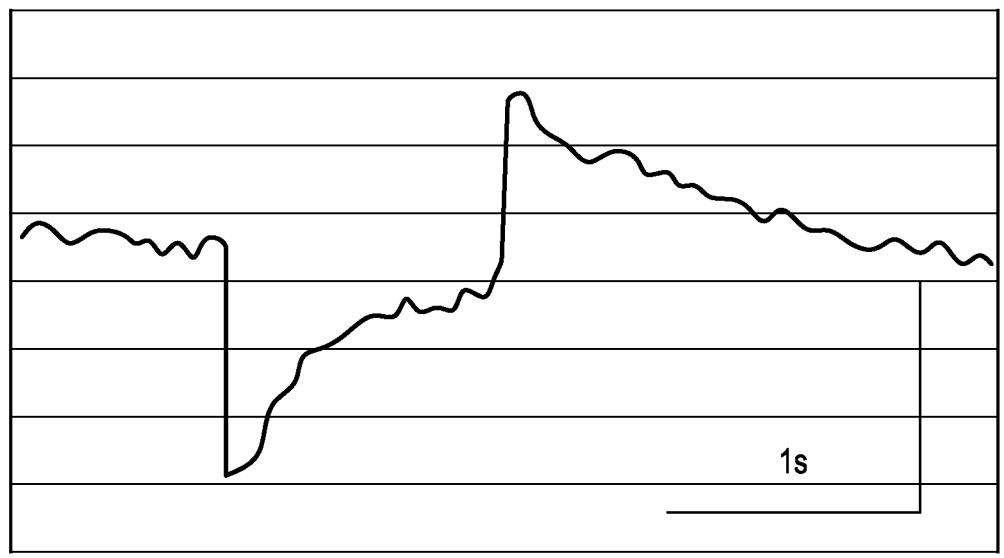
FIG. 13A is a plot showing the change in fluorescent intensity of the CHO cell shown in FIG. 12 in response to electrophysiological stimulation of the cells using a patch-clamp method in a whole-cell mode. X-axis of reference time scale bar (inset) shows duration of 1 second.
Figure 13B:
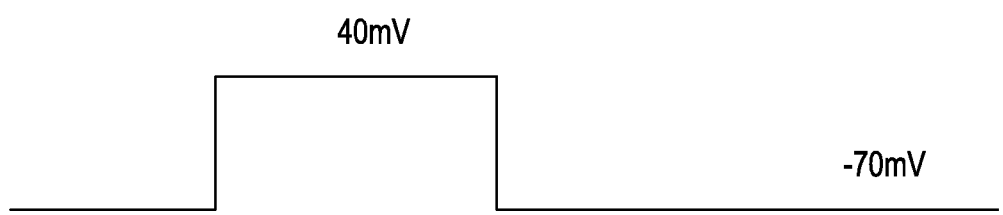
FIG. 13B is a trace that represents the corresponding voltage stimulation protocol along the same time scale as FIG. 13A.

A standard electrophysiological protocol was used to directly command the cell membrane potential via a voltage-step depolarization delivered through a patch pipette to a cell in whole-cell mode. FIG. 12 shows a CHO cell 1200 that is being electrically stimulated with an electrode 1202. The fluorescent image of a CHO cell labeled with a quantum dot-based voltage sensor is shown in FIG. 9. FIG. 13 shows the change in fluorescence intensity of cells labeled with quantum dot-based voltage sensors in response to electrophysiological stimulation. The voltage stimulation protocol along the same time scale is shown in FIG. 13A.

During these experiments it was observed that the fluorescence response of nanocrystal-based voltage sensors correlated with electrophysiological recordings of the membrane potential. The results demonstrate that nanocrystal-based voltage sensors exhibit voltage sensitivity within the physiological membrane potential range and bring the added advantages to cellular imaging afforded by unique optical properties of semiconductor nanoparticles such as photostability, large Stokes shift, and multiplexing capability.

Example 3

Quantum Dot-Based Activation Platforms

A light-controlled activation platform is described for remote reversible manipulation of the membrane potential. The described materials and methods provide an alternative to passive monitoring of the cell functional activity, and provide the ability to non-invasively manipulate the membrane potential of cells, which is vital for understanding their development, communications and fate. Traditional non-physiological methods rely most commonly on pharmacological intervention via addition of "high K+" solution or pharmacological channel openers or direct stimulation of cells with microelectrodes. These non-physiological methods, however, can have serious shortcomings, including the lack of control of the membrane potential, irreversibility of elicited changes, and low temporal resolution.

The alternative approach provided herein uses light to trigger remote reversible manipulation of the membrane potential in a temporally precise and spatially resolved manner. Light is being increasingly adopted in both in vitro and in vivo applications. For example, light is used to manipulate genetically-encoded light-sensitive proteins, such as naturally occurring (channelrhodopsin, ChR2) or chemically modified ion channels, despite concerns regarding the need for a high level of expression of exogenous proteins in the cells of interest. Light stimulation of these and other types of cells (e.g., in the presence of nanocrystals) at the levels required for stimulation of the nanocrystals described herein was shown to have no effect on cell potential (data not shown.)

Figure 14:
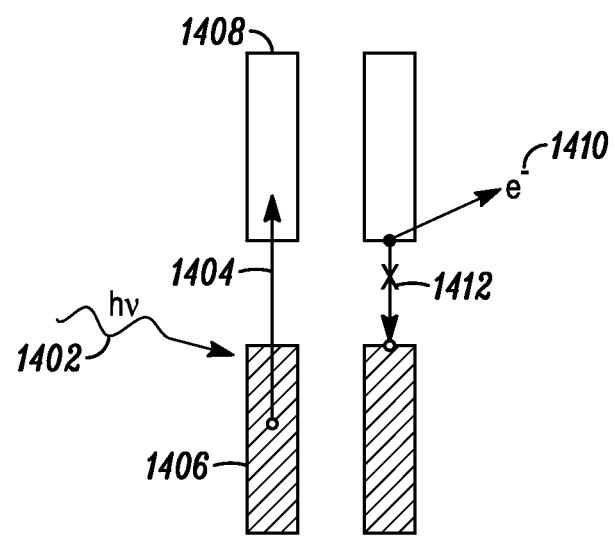
FIG. 14 shows the proposed mechanism of action for a quantum dot nanocrystal-based voltage sensor that releases an electron upon irradiation with light.

Quantum dots present an alternative solution for light-controlled electrical activation of live cells. As discussed above, upon exposure to the light, quantum dots can generate free electrons and holes. The fate of these free charge carriers is to 1) radiatively recombine and emit light or 2) to escape and create an electrical current. Referring to FIG. 14, the absorption of a photon 1402 with energy higher than the band gap 1404 between the HOMO valence band 1406 and the LUMO conduction band 1408 of a quantum dot forms an electron-hole pair. If one or more of the free charge carriers is released (i.e. an electron (e−) 1410) then radiative recombination to emit light cannot occur (depicted as forbidden transition 1412).

Just as quantum dot nanocrystals have been engineered to maximize radiative recombination (fluorescence), nanocrystal particles are described herein which have been engineered to maximize current. When such quantum dots are formed into a three-dimensional array, strong electronic coupling between them leads to excitons with a longer lifetime and facilitates the collection and transport of photogenerated free charge carriers. The rates of photogenerated carrier separation, transport, and interfacial transfer across the contacts to the biological interface must all be fast to maximize the output. Important to the improvement of photo-conversion efficiency are the efficiency of charge separation and facilitation of the charge transport through the nanostructured platform.

To address the need for a light-controlled activation platform for biological applications, the photoelectronic properties of quantum dots can be exploited to develop a nanostructured biocompatible interface that is composed of stacks or layers of semiconductor nanocrystals coated with an adhesion layer. To prepare multilayered quantum dot thin films for cell activation, a layer by layer (LBL) deposition method (such as described in Examples 9 and 10) was used to assemble quantum dots on glass coverslips. Studies were conducted to determine if an adhesion substrate (e.g., a layer formed of poly-L-lysine) improved attachment of the cells to the activation platform. Initial experiments using layers of nanocrystals without the adhesion layer (or adhesion substrate) demonstrated that 10% or less of the cells attached to the nanocrystal layers. This low level of cell availability rendered the assay unworkable. Inclusion of an adhesive layer permitted cells to attach to the substrate, with the additional benefit of decreasing the distance between the cells and the activation material. Imaging studies showed that the adhesion molecules described herein are in uniform, tightly associated contact with the substrate. Further, the addition of an adhesion layer between the nanocrystals and the cells did not interfere with the energy transfer between the nanocrystals and the cells (e.g., by forming an insulating layer). High adhesion of cells (e.g., cell adhesion of 90% or more) to the activation platform was crucial, as the efficiency of conversion of light energy to changes in cell membrane potential was inversely dependent on the distance between the substrate and cells. Furthermore, adhesion molecules are critical for full differentiation, spreading, attachment of most cells, especially neurons. When these nanocrystals were placed in close proximity to a cell and illuminated by visible light, the cumulative electromagnetic field generated by photo-excited nanocrystals (or light-induced current) modulated the cell membrane potential. Thus, this nanocrystal-based light-controlled activation platform allowed one to stimulate cells physiologically (electrical field) and repeatedly. Moreover, this activation platform was compatible with any fluorescent readout, since due to the broad absorption spectrum, semiconductor nanocrystals can be excited by any light shorter than their emission wavelength.

Example 4

Light Controlled Activation of Cells

An activation platform such as described in Example 3 was used in various light-controlled experiments designed to monitor the effect of the activation platform on the membrane potential of different types of cells.

Figure 17:
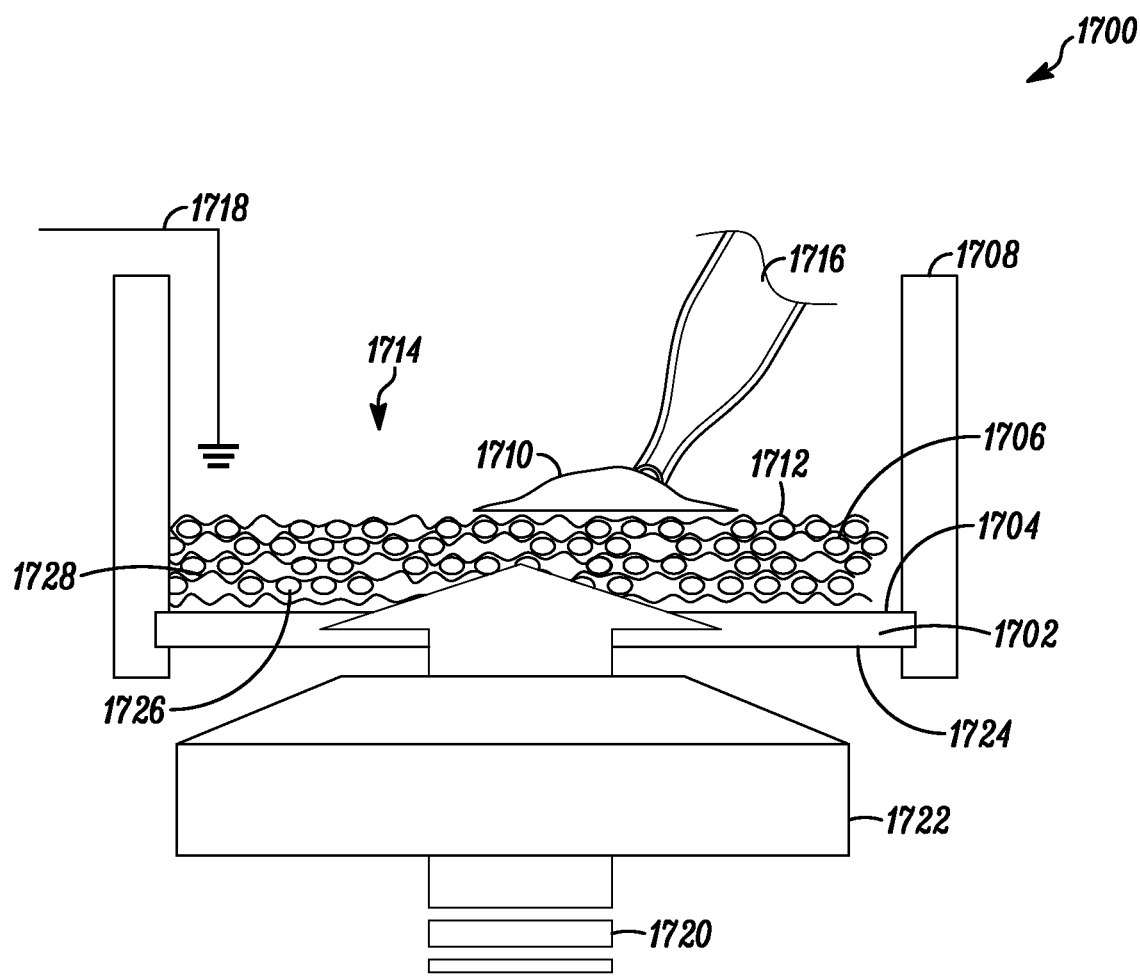
FIG. 17 is a schematic presentation of an experimental patch-clamp scheme.

A current-clamp configuration was used to record the changes in membrane potential elicited by light using excitable and non-excitable cells. FIG. 17 shows an exemplary current-clamp configuration 1700 including a transparent coverslip 1702 having immobilized on its surface 1704 an activation platform 1706 bounded by walls 1708. The activation platform is formed of alternating layers of quantum dots 1726 and polymer 1728 (e.g., poly(diallyldimethylammonium chloride) (PDDA)). A cell 1710 resides on the top surface 1712 of the activation platform 1706. An aqueous medium (e.g., water, buffer, or cell culture media) 1714 covers activation platform 1706 and cell 1710. An electrode 1716 is inserted into cell 1710. A reference electrode 1718 is immersed in aqueous medium 1714. Depolarization of cells is achieved by passing "activation" light 1720 from a mercury lamp (not shown) through an objective 1722 such that the light impinges the underside 1724 of transparent coverslip 1702. Typically, short pulses of light (e.g., between 350 and 450 nm using either broad band excitation from an arc lamp or narrow band from a laser source) are used to irradiate the activation platform. The light travels through the transparent coverslip and irradiate the activation platform 1706. Excitation of the quantum dots 1726 contained within activation platform 1706 triggers changes in the membrane potential and action potential (mV) for cell 1710.

Figure 16:
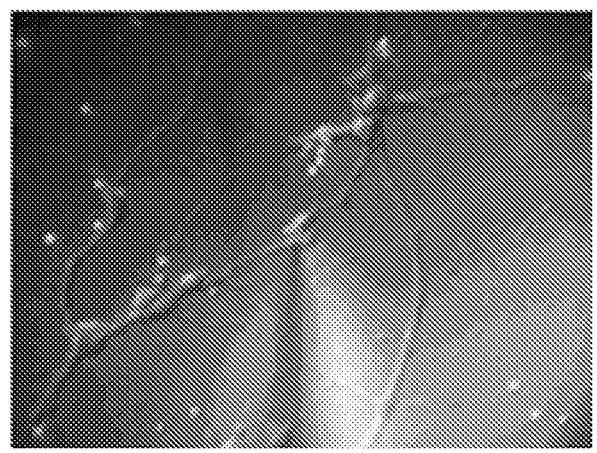
FIG. 16 is a bright field image of hippocampal neurons cultured on a quantum dot nanocrystal-based activation coverslip with a stimulating giga seal patch pipette attached.
Figure 18:
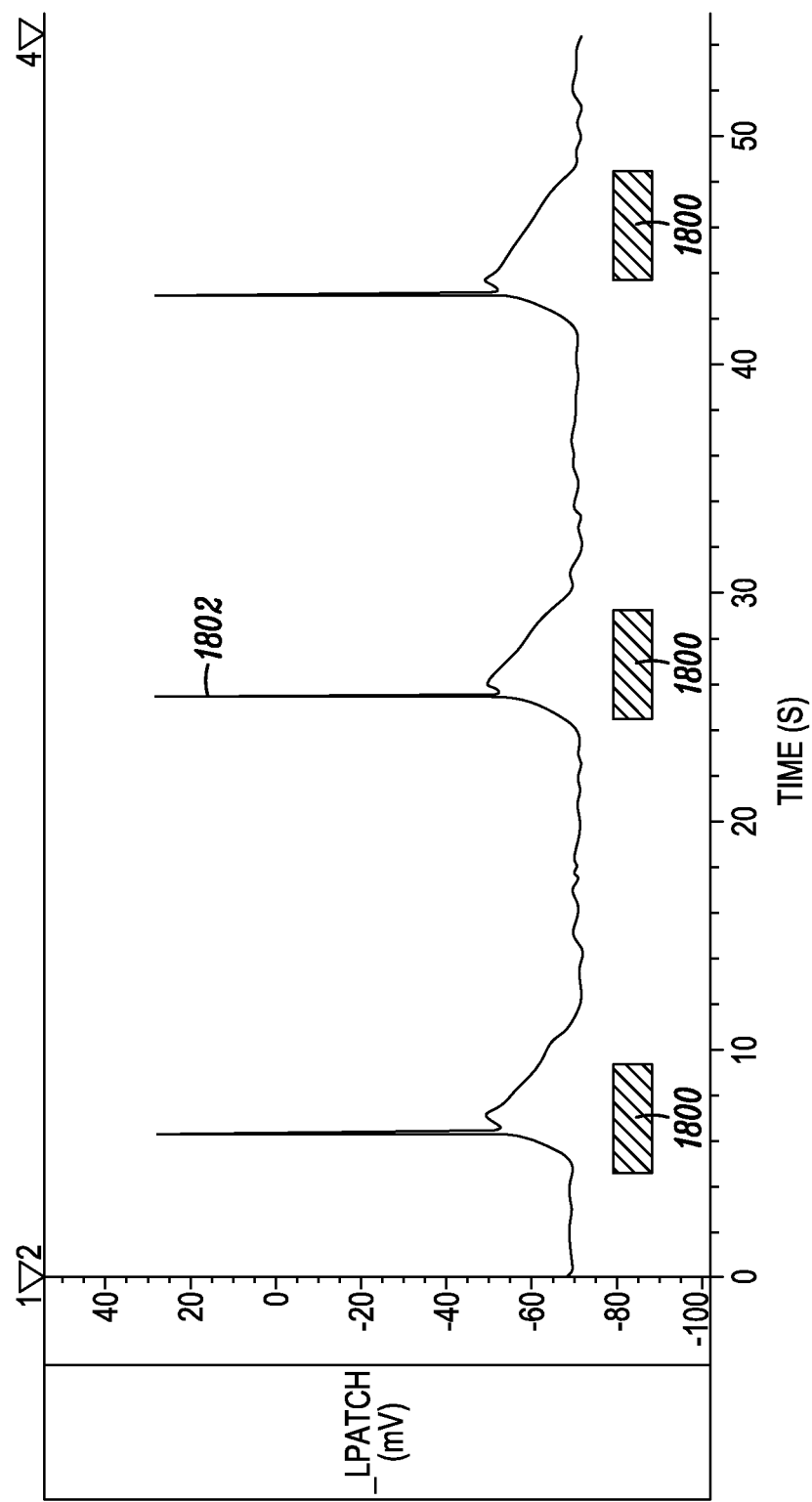
FIG. 18 shows changes in membrane potential and action potential over time upon repeated triggering by light.
Figure 19:
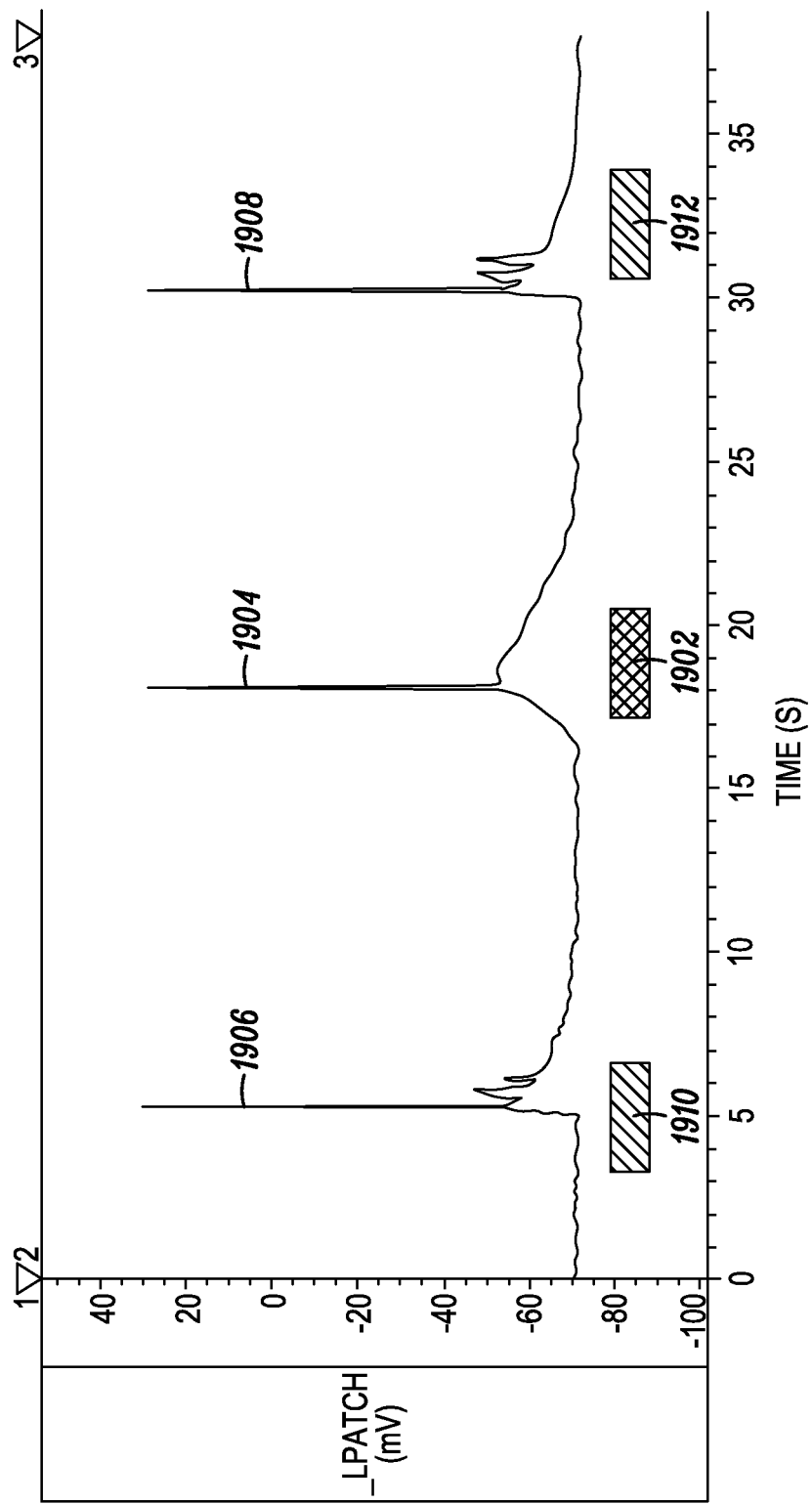
FIG. 19 shows changes in membrane potential over time using alternating electrical and optical excitation.

A multilayer activation platform was used to assay the effect of quantum dots on excitable and non-excitable cells types (CHO cells, RBL cells, NG108 cells, hippocampal neurons). Cells were cultured on poly-L-lysine-coated nanocrystal-layered glass coverslips for 3 to 14 days. FIG. 16 shows a bright-field, pseudo phase image of a primary culture of hippocampal neurons cultured on a quantum dot-based activation coverslip. Over the course of these experiments, no adverse effects of nanocrystals on cellular morphology, differentiation or physiological responses were observed. FIG. 18 shows the changes in membrane potential upon repeated triggering of a primary culture of hippocampal neurons cultured on a quantum dot-based activation coverslip by light pulses 1800. Depolarizing responses in cells were proportional to the light intensity and their absorption response (e.g. wave length dependency) directly paralleled the expected absorption properties of nanomaterials used in the activation platform. Light exposure of neurons cultured on activation platform coverslips resulted in a membrane depolarization that triggered the action potential 1802. FIG. 19 shows the change in membrane potential elicited by alternative generation of action potentials in NG108 cells cultured on a quantum dot-based light-controlled activation platform using first current pulse 1910 injection (through a patch clamp electrode as diagramed in FIG. 17), a light pulse 1902, and a second current pulse 1912. Light exposure 1902 resulted in membrane depolarization that triggered action potential 1904. The resulting action potential 1904 generated by the light pulse 1902 was comparable to the action potentials 1906 and 1908 elicited using current pulse injection 1910 and 1912. The timing and scale of the action potentials were nearly identical, regardless of the source of the stimulation, though the recovery (repolarization) of the optically induced stimulation showed some slight differences.

Upon light illumination, the activation platform demonstrated the ability to repeatedly depolarize the membrane in non-excitable cells (CHO cells, RBL cells) (data not shown) and generated action potentials in excitable cells, such as NG108 cells and primary culture of hippocampal neurons, with the only limitation being the giga-seal stability. The failure of a giga-seal electrode over extended periods, with a limited utility measured in hours, further substantiates the utility of the non-invasive, optical based approaches described herein.

Example 5

Integrated Optical Assay to Monitor Cellular Activity

An integrated optical assay is described that combines optical stimulation (via activation platform coverslips) and optical recording of cellular activity. Changes in intracellular calcium concentration were measured (via a calcium indicator dye) to monitor the effect of light-triggered activation of cells.

Figure 20A:
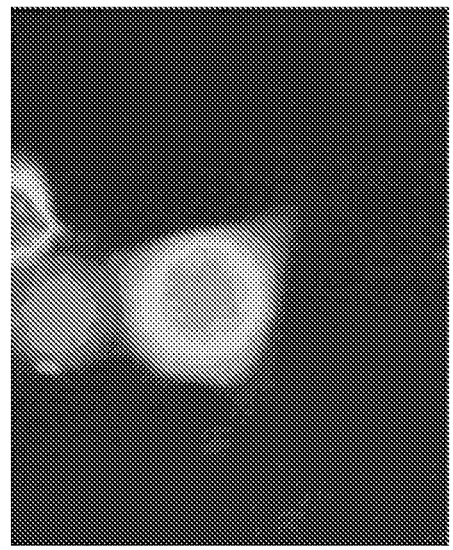
FIG. 20 shows fluorescent images of NG108 cells loaded with a fluorescent calcium indicator, before (A) and after (B) an activation light pulse (380 nm).
Figure 20B:
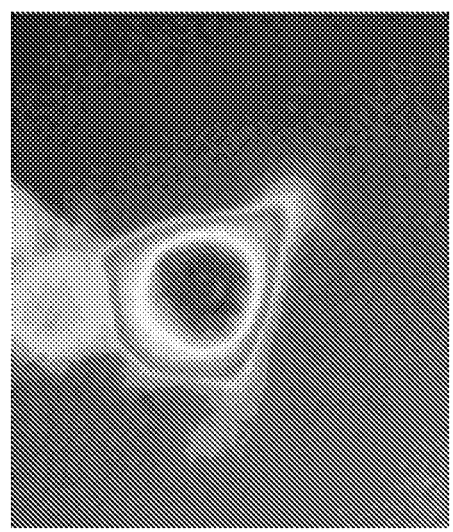
Figure 21:
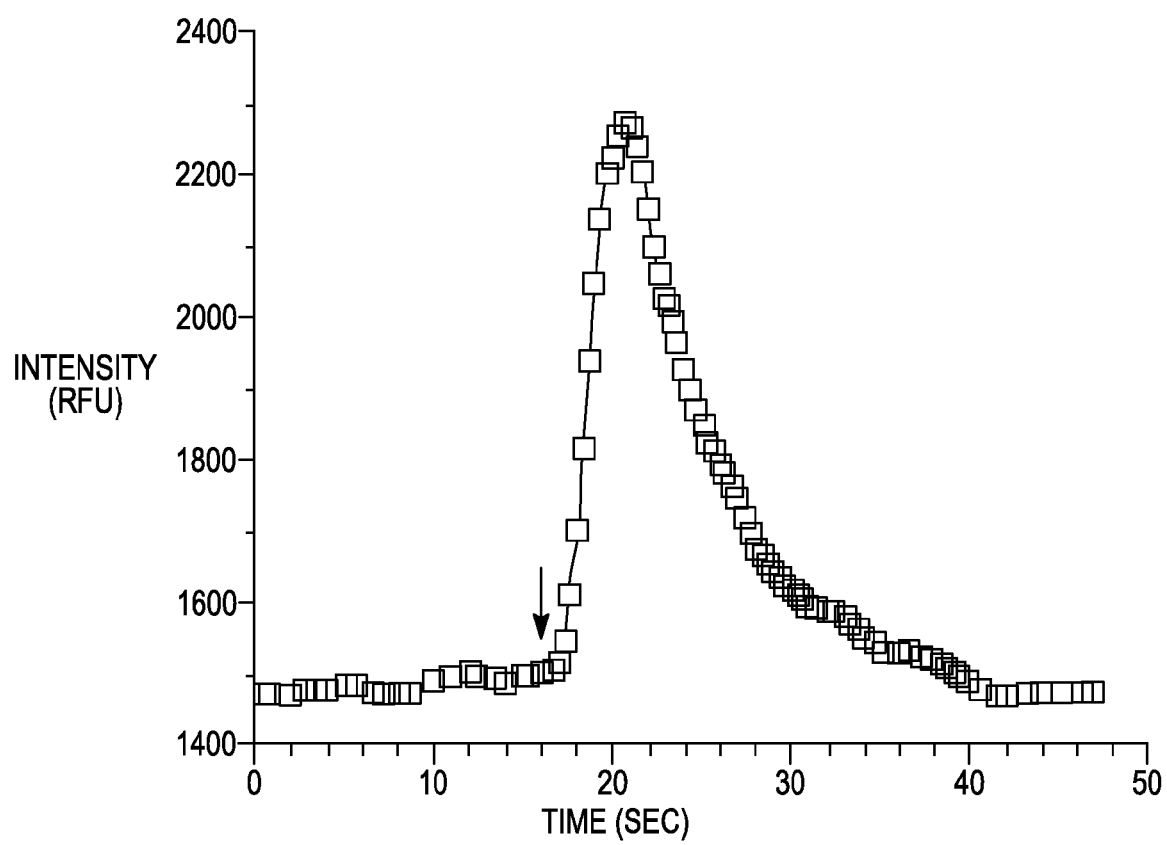
FIG. 21 is a plot showing the fluorescent intensity of Fluo-4 calcium indicator over time following an activation light pulse of 380 nm (identified with an arrow). The plot reflects changes in intracellular calcium concentration as a result of light-triggered action potential.

A glass coverslip having immobilized on its surface an activation platform, such as described in Examples 1-4, was used in the experiment. Since these nanocrystal-coated activation platforms were transparent, they were compatible with various optical interrogation methods. NG108 cells were loaded with Fluo-4 (a fluorescent calcium indicator available from Life Technologies Corporation; Carlsbad, Calif.) using standard protocols. FIG. 20 shows bright-field images of the loaded NG108 cells before (A) and after (B) an activation light pulse. The Fluo-4 indicator fluoresces subsequent to irradiation of the activation platform, indicating an increase in intracellular calcium levels. FIG. 21 shows the change in fluorescence intensity of the Fluo-4 indicator dye before and after an activation light pulse (380 nm) (at a time identified by arrow) and represents the calcium influx in NG108 cells through voltage-gated calcium channels involved in the light-triggered action potential. The results indicated that intracellular calcium concentration increased as a result of light-triggered electrical depolarization of the cell through the conversion of light to electrical field by the nanomaterial coating and subsequent opening of voltage dependent calcium currents. The increased fluorescence shown in FIG. 20B is due to the calcium entering the cell and binding this fluorogenic probe. This example shows that optically initiated depolarization yielded results identical to those obtained using a patch clamp experiment, where depolarization is electronically recorded.

Example 6

Heterogeneous Activation of Neuronal Network

Figure 22A:
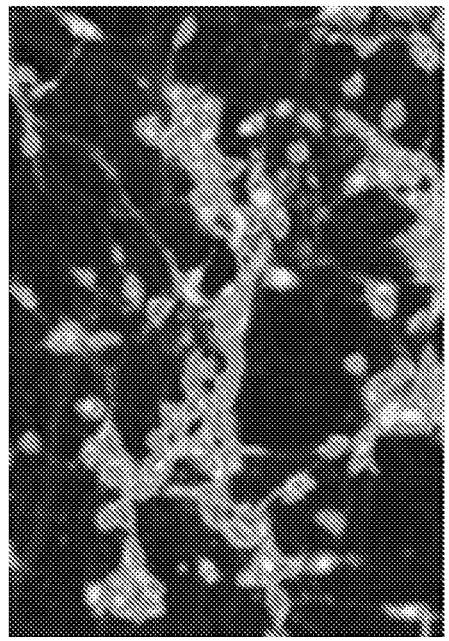
FIG. 22 shows wide field fluorescent images of hippocampal neurons loaded with Fluo-4 calcium indicator before (A) and after (B) an activation light pulse (380 nm).
Figure 22B:
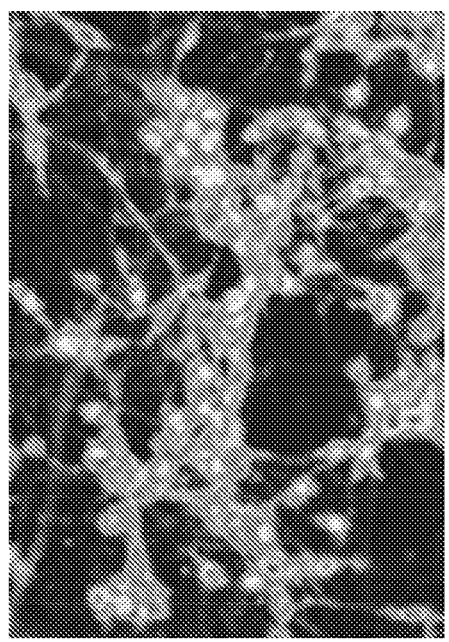
Figure 23:
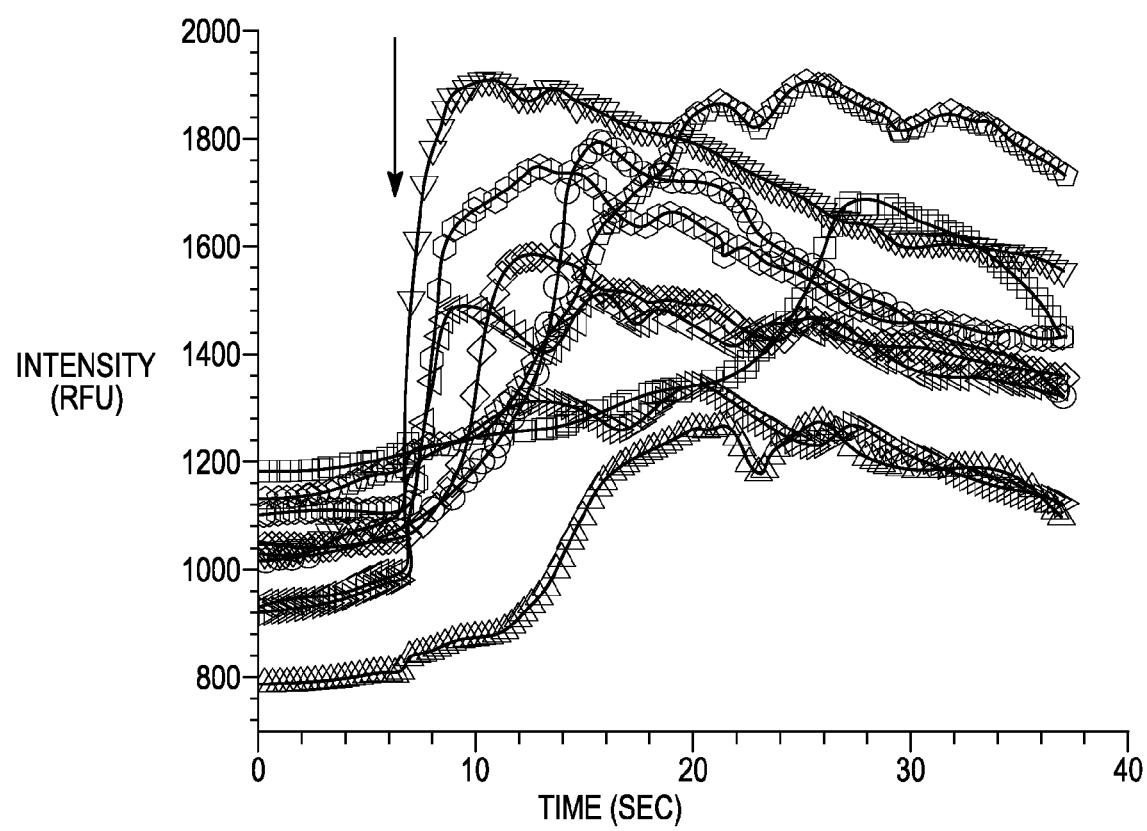
FIG. 23 shows a plot of fluorescent intensity of Fluo-4 calcium indicator over time as a result of light-triggered activation of a neuronal network. The plot illustrates changes in intracellular calcium concentration in several neurons as a result of light-triggered activation of the neuronal network.

A primary culture of hippocampal neurons were loaded with Fluo-4 calcium indicator as described in Example 5. FIG. 22 shows images of Fluo-4 loaded hippocampal neurons before (A) and after (B) an activation light pulse. The activation light pulse causes an increase in intracellular calcium levels that induces a change in the fluorescence properties of the Fluo-4 indicator. As shown in FIG. 22B, activated cells cause the indicator to fluoresce. FIG. 23 is a plot showing the change in Fluo-4 fluorescence intensity over time and reflects changes in intracellular calcium concentration for neurons as a result of light-triggered activation of the neuronal network. The activation light pulse (380 nm) occurs at a time identified with an arrow. The data demonstrates that light excitation inducts the heterogeneous activation of the neuronal network. Here some neurons were activated directly by light (note the fast-rising calcium flux), whereas other neurons were activated indirectly through inter-neuronal connections (note delayed and, sometimes, multi-peak calcium flux pattern). The data in both FIG. 21 and FIG. 23 demonstrate that the intracellular calcium concentration increases as a result of light triggered activation of cells using an activation platform. The data further demonstrates that a nanocrystal-based activation platform can be used to deliver a physiologically relevant activation stimulus compatible with optical methods of registration.

Example 7

Preparation of Coated Nanocrystals

Trisoctylphosphine oxide (TOPO) coated CdSe nanocrystals prepared according to Example 1 of U.S. Pat. No. 6,322,901 were mixed with thioglycerol in large excess. The mixture was stirred overnight at 70° C. Next morning isopropyl alcohol was added to precipitate the nanocrystals. The nanocrystals were re-dispersed in 0.1M NaHCO$_3$, followed by the addition of isopropyl alcohol to precipitate the nanocrystals again to remove any residual thioglycerol in the solution. 0.1M NaHCO$_3$ was added to disperse the nanocrystals. The nanocrystals can be further purified using an ultrafiltration filter. The identical procedure was used to treat TOPO coated CdSe nanocrystals with thioglycolic acid or lipoic acid.

Example 8

Preparation of Polyethylenimine Coated Nanocrystals

Trisoctylphosphine oxide coated CdSe nanocrystals prepared according to Example 1 of U.S. Pat. No. 6,322,901 were mixed with pyridine and heated at 110° C. for 5 hours with stirring. Polyethylenimine was dissolved in ethanol at a weight concentration from 5 to 15%. The polymer solution then was added to the nanocrystal solution and stirred overnight at 70° C. Next morning, excess solvents were removed using a rotary evaporator. To the remaining nanocrystals, deionized distilled water was added to disperse the nanocrystals. Finally, the nanocrystals were purified using an ultrafiltration filter to remove excess polymer.

Example 9

Preparation of Nanocrystal Film

LBL Method

Glass coverslips were cleaned in 0.5M NaOH solution in a sonication bath. The cleaned coverslips were rinsed thoroughly in deionized, distilled water and immediately immersed into a poly(diallyldimethylammonium) (PDDA) solution. After 10 minutes, the coverslips were taken out of the PDDA solution and rinsed thoroughly in deionized, distilled water to remove any unbound PDDA. After rinsing, the coverslips were immersed into a thioglycerol-coated water-soluble CdSe nanocrystal solution to deposit a layer of quantum dot film. After 10 minutes, the coverslips were taken out of the CdSe solution and rinsed thoroughly in water to remove any unbound CdSe nanocrystals. Additional layers of quantum dot films can be deposited by repeated dipping alternately into PDDA and CdSe solutions, until the desired film thickness is achieved.

Example 10

Preparation of Layered Nanocrystal Film

LBL Method

Glass coverslips were cleaned and treated with PDDA, as described in Example 9. After rinsing, the coverslips were immersed into a thioglycolic acid-coated water-soluble CdSe nanocrystal solution to deposit the first layer of quantum dot film. After 10 minutes, the coverslips were taken out of the CdSe-thioglycolic acid solution and rinsed thoroughly in water to remove any unbound nanocrystals. After rinsing, the coverslips were deposited into a polyethylenimine-coated water-soluble CdSe nanocrystal solution to deposit a layer of positively charged quantum dot film. Additional layers of quantum dots can be deposited by alternating deposition of oppositely charged water-soluble nanocrystals.

Example 11

Polylysine Treatment of Activation Platforms

After the preparation of quantum dot films via a layer-by-layer (LBL) method, as described in Examples 9 and 10, the coverlips were immersed into a solution of polylysine for 30 minutes. The coverslips were then taken out of the polylysine solution, rinsed thoroughly in water to remove any unbound materials and dried under nitrogen. Alternatively, depending on the surface charges of the quantum dot films, the coverslips were first immersed into polystyrene sulfonate solution for 10 minutes, followed by washing the coverslips in water, and then dipped into polylysine solution.

Example 12

Preparation of ITO Activation Platform

A method is described for deposition of quantum dots on the surface of an indium tin oxide (ITO) substrate. An ITO substrate is dipped into a solution of water and a polycationic polymer (e.g., PDDA). Since ITO has a negatively charged surface, the cationic polymer can adhere to the ITO and render the surface positively charged. The ITO substrate is washed with deionized water and then dipped into a solution of negatively charged CdTe nanoparticles in water (e.g., dihydrolipoic acid (DHLA) capped CdTe). The negative particles will adhere to the cationic polymer surface on the substrate and render the surface negatively charged. This process can be repeated to generate an assembly having multiple nanoparticle layers. The ITO-based activation platform can, optionally, be linked into a circuit to create a sustained flow of charge.

Example 13

Spin Coating of Quantum Dot Film

Electrophoresis-grade agarose was dissolved in 0.1M NaHCO$_3$ at 1% w/v concentration on a hot plate. After the agarose solution became completely optical clear, a small amount of thioglycolic acid-coated water-soluble CdSe nanocrystals were added to the agarose solution with stirring. Still hot, the agarose solution was poured or spin-coated onto a chemically treated glass coverslip. After air dry at ambient temperature, a thin agarose film embedded with quantum dots was formed on the coverslip.

Example 14

Preparation of InP Nanocrystals

An InP core was prepared as follows. In a reaction flask under inert atmosphere, 0.88 g of indium acetate (In(OAc)3), 0.254 g oleic acid, and 14.8 g of 1-octadecene (ODE) that was purified to remove oxygen and water were combined. The contents of the flask were heated to 260° C. while a flow of nitrogen was directed through the flask to remove acetic acid as it formed. After 5 minutes at this temperature, the flow of nitrogen was stopped. A 0.02 M solution of tris(trimethylsilyl)phosphine ($TMS_3P$) in ODE was prepared by adding 0.45 g of $TMS_3P$ to 7.101 g ODE. The contents of the flask were heated to 300° C. At 300° C., the $TMS_3P$ solution was quickly injected into the mixture. Nanocrystal formation was monitored by standard methods (achieving a desired fluorescence emission wavelength) until InP cores of the desired particle size was obtained, and the reaction was then cooled to room temperature.

Example 15

Preparation of CdSe Nanocrystals

TDPA (0.549 g), TOPO (6.000 g), and a magnetic stir bar were added to a clean, dry 50 mL three-neck round bottom flask. The first port of the flask was equipped with a gas inlet adapter to allow for evacuation and nitrogen refill, the second port was equipped with a temperature probe attached to a temperature control device, and the third port was fitted with a rubber septum. The flask was evacuated, refilled with nitrogen gas, and maintained under a nitrogen blanket. TOP (3.6 mL) and 1.972 g of Cd-TOP solution (containing cadmium acetate dissolved in TOP at a concentration of 0.5 moles of cadmium per kg solution) were added. A needle was inserted into the septum on the third port. The mixture was heated to 260° C. and held at that temperature for 20 minutes. The needle was removed and the reaction flask was heated to 355° C. During this heating step, diphenylphosphine (0.030 mL) was added, and at 340° C., 1.4 mL of TOP-Se (1M selenium shot in TOP) was added. Aliquots were removed every 30 seconds to determine the current emission maximum. The reaction was halted by addition of 4.0 mL of room-temperature TOP.

Example 16

Preparation of a CdSe Core with a Thin CdS Shell

TOPO (3.383 g) and a magnetic stir bar were added to a 50 mL three-neck round bottom flask. Ports 1, 2, and 3 were capped as described in Example 1. The flask was evacuated and refilled with nitrogen gas. Under vacuum and with constant stirring, the TOPO was heated to 180° C. for 1 hour. The flask was refilled with nitrogen gas and allowed to cool to 100° C. before TOP (3.4 mL) was added. Ethanol (21.3 mL) and a sample of the cores prepared in Example 15 (10.7 mL warmed to 50° C.) were added to a 60 mL centrifuge tube. The mixture was centrifuged, the supernatant was discarded, and the pellet was redispersed in hexanes. The dispersion was then added to the reaction flask at 100° C. A vacuum was applied to remove the hexanes leaving the nanocrystals dispersed in TOPO and TOP. Decylamine (2.8 mL) was added to the reaction flask. In a second flask, a mixture of 3.905 g of Cd-TOP solution described in Example 15, TDPA (2.730 g), and TOP (2.7 mL) were momentarily heated to 250° C. and then cooled to 100° C. under a nitrogen atmosphere. After 45 minutes, 2.5 mL of the cadmium acetate/TDPA/TOP solution was added to the cores. The reaction flask was heated to 230° C. and 3.9 mL of a solution containing TOP (2.926 g) and hexamethyldisilthiane (0.203 g) was added drop-wise over a period of three hours. If thinner shells were desired, the dropwise addition was stopped at 1 or 2 hours, for example. Aliquots were withdrawn from the reaction periodically to track the emission properties.

All of the compositions and/or methods and/or processes and/or apparatus disclosed and claimed herein can be made and executed without undue experimentation in light of the present disclosure. While the compositions and methods of this invention have been described in terms of preferred embodiments, it will be apparent to those of skill in the art that variations may be applied to the compositions and/or methods and/or apparatus and/or processes and in the steps or in the sequence of steps of the methods described herein without departing from the concept and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the scope and concept of the invention.

The invention claimed is:

1. A composition for monitoring and manipulating cellular transmembrane potentials, comprising:
   a. a substrate; and
   b. an activation platform is disposed on a surface of the substrate, wherein the activation platform comprises multiple layers of immobilized nanocrystals and at least one polymer layer, wherein said polymer layer comprises a polymer selected from agarose, polymethyl methacrylate, polyacrylamide and poly(diallyldimethylammonium chloride), that is interposed between adjacent layers of immobilized nanocrystals, wherein at least one layer of immobilized nanocrystals comprises positively charged nanocrystals, wherein each positively charged nanocrystal comprises a surface coating that comprises a positively charged compound, wherein the multiple layers of immobilized nanocrystals are arranged to facilitate the flow of electrons through the activation platform, and wherein the composition is configured for monitoring and manipulating cellular transmembrane potentials.

2. The composition of claim 1, wherein the nanocrystals are semiconductor nanocrystals.

3. The composition of claim 2, wherein the semiconductor nanocrystals each comprise a semiconductor core and a semiconductor shell material surrounding the core.

4. The composition of claim 1, wherein the positively charged nanocrystals each comprise a semiconductor core and a surface coating that is bound to the core.

5. The composition of claim 4, wherein the surface coating comprises a hydrophilic compound.

6. The composition of claim 1, wherein the surface coating comprises a compound selected from the group consisting of polyethylenimine, cysteamine, polyallylamine, histidine, polyhistidine, lysine, polylysine, and poly(diallyldimethylammonium chloride).

7. The composition of claim 1, wherein the activation platform further comprises an adhesion substrate that includes a material selected from poly-L-lysine, fibronectin, collagen, elastin, hyaluronic acid, laminin, matrigel, lectins, antibodies to cellular membrane proteins, and RGD peptides or their progeny.

8. The composition of claim 1, wherein the activation platform comprises two or more types of nanocrystals, wherein the two or more types of nanocrystals have different optical properties.

9. The composition of claim 1, wherein the nanocrystals are water-dispersible.

10. The composition of claim 4, wherein the activation platform is covered by a cell adhesion layer.

11. The composition of claim 1, wherein the activation platform further comprises at least one layer of negatively charged nanocrystals.

12. The composition of claim 11, further comprising alternating layers of positively and negatively charged nanocrystals.

13. The composition of claim 11, wherein the negatively charged nanocrystals each comprise a semiconductor core and a surface coating that is bound to the core, wherein the surface coating comprises a negatively charged compound.

14. The composition of claim 1, further comprising a cell attached to a surface of the activation platform.

15. The composition of claim 14, wherein the flow of electrons through the activation platform modulates the membrane potential of the cell attached to the surface of the activation platform.

16. The composition of claim 1, wherein the activation platform is configured to conduct electrical current.

17. A composition, comprising:
a. a substrate;
b. an activation platform configured to conduct electrical current, wherein the activation platform is disposed on a surface of the substrate, wherein the activation platform comprises multiple layers of immobilized semiconductor nanoparticles, and at least one polymer layer interposed between adjacent layers of immobilized nanocrystals, wherein said polymer layer comprises a polymer selected from agarose, polymethyl methacrylate, polyacrylamide and poly(diallyldimethylammonium chloride), wherein at least one layer of immobilized nanocrystals comprises positively charged nanocrystals, wherein each positively charged nanocrystal comprises a surface coating that comprises a positively charged compound, wherein the nanoparticles are arranged to facilitate the flow of electrons through the activation platform; and
c. a cell attached to a surface of the activation platform, wherein the flow of electrons through the activation platform modulates the membrane potential of the cell.

* * * * *